United States Patent
Green

(10) Patent No.: US 6,767,733 B1
(45) Date of Patent: Jul. 27, 2004

(54) PORTABLE BIOSENSOR APPARATUS WITH CONTROLLED FLOW

(75) Inventor: Larry R. Green, Tacoma, WA (US)

(73) Assignee: PriTest, Inc., Redmond, WA (US)

( * ) Notice: Subject to any disclaimer, the term of this patent is extended or adjusted under 35 U.S.C. 154(b) by 186 days.

(21) Appl. No.: 09/974,089

(22) Filed: Oct. 10, 2001

(51) Int. Cl.⁷ .............................. C12M 1/34; C12Q 1/00
(52) U.S. Cl. ..................... 435/288.5; 435/4; 435/287.2; 435/288.7; 422/82.11; 436/164
(58) Field of Search .............. 435/4, 34, 287.2, 435/287.3, 289.9, 288.3–288.5, 288.7; 436/44, 47, 48, 49, 164, 165, 172, 180; 422/62, 65, 67, 68.1, 82.05, 82.11, 100, 102; 385/12

(56) References Cited

U.S. PATENT DOCUMENTS

| | | |
|---|---|---|
| 3,973,129 A | 8/1976 | Blumberg et al. |
| 4,019,820 A | 4/1977 | Kopito et al. |
| 4,829,010 A | 5/1989 | Chang |
| 5,100,777 A | 3/1992 | Chang |
| 5,128,528 A | 7/1992 | Heninger |
| 5,259,391 A | 11/1993 | Altshuler et al. |
| 5,287,272 A | 2/1994 | Rutenberg et al. |
| 5,364,790 A | 11/1994 | Atwood et al. |
| 5,370,842 A | 12/1994 | Miyazaki et al. |
| 5,414,258 A | 5/1995 | Liang |
| 5,512,492 A | 4/1996 | Herron et al. |
| 5,654,413 A | 8/1997 | Brenner |
| 5,763,189 A | 6/1998 | Buechler et al. |
| 5,779,978 A | 7/1998 | Hartmann et al. |
| 5,827,748 A | 10/1998 | Golden |
| 5,838,435 A | 11/1998 | Sandison |
| 5,858,804 A | 1/1999 | Zanzucchi et al. |
| 5,922,593 A | 7/1999 | Livingston |
| 5,922,617 A | 7/1999 | Wang et al. |
| 5,963,368 A | 10/1999 | Domanik et al. |
| 6,006,991 A | 12/1999 | Faklis et al. |
| 6,049,421 A | 4/2000 | Raz et al. |
| 6,118,126 A | 9/2000 | Zanzucchi |
| 6,137,117 A | 10/2000 | Feldstein et al. |
| 6,140,044 A | 10/2000 | Besemer et al. |
| 6,146,593 A | 11/2000 | Pinkel et al. |
| 6,171,238 B1 | 1/2001 | Klimes et al. |
| 6,192,168 B1 | 2/2001 | Feldstein et al. |
| 6,242,267 B1 | 6/2001 | Herron et al. |
| 6,251,616 B1 | 6/2001 | Barbera-Guillem et al. |
| 6,258,593 B1 | 7/2001 | Schembri et al. |
| 6,258,606 B1 | 7/2001 | Kovacs |

(List continued on next page.)

FOREIGN PATENT DOCUMENTS

| | | |
|---|---|---|
| JP | 02002150478 A | 5/2002 |
| WO | PCT/US02/32359 | 1/2003 |

OTHER PUBLICATIONS

Dodson, James M., et al. "Fluidics Cube for Biosensor Miniaturization," *Anal. Chem.*, 2001, 73, pp. 3776–3780.

*Primary Examiner*—William H. Beisner
(74) *Attorney, Agent, or Firm*—Richard A. Nakashima; Faegre & Benson

(57) ABSTRACT

The present invention concerns a portable, reliable and sensitive biosensor apparatus. In certain embodiments, the apparatus incorporates a fluidic cube, comprising a vent cap, vent cap isolator, cube body, waveguide and stage. In preferred embodiments, the fluidic cube further comprises a fluid manifold. In more preferred embodiments, the fluidic cube comprises one or more sample channels that are designed to increase fluid mixing through the use of baffles. The biosensor is designed to simultaneously process multiple samples for a variety of analytes. In certain embodiments, the biosensor is designed to operate as a compact, stand-alone automated unit that can reliably analyze environmental, clinical, veterinary, pathologic or medical samples under adverse field conditions.

19 Claims, 17 Drawing Sheets

U.S. PATENT DOCUMENTS

| | | |
|---|---|---|
| 6,277,627 B1 | 8/2001 | Hellinga |
| 6,277,628 B1 | 8/2001 | Johann et al. |
| 6,287,871 B1 | 9/2001 | Herron et al. |
| 6,289,144 B1 | 9/2001 | Neuschäfer et al. |
| 6,294,392 B1 | 9/2001 | Kuhr et al. |
| 6,297,059 B1 | 10/2001 | Song et al. |
| 6,303,929 B1 | 10/2001 | Oshima et al. |
| 6,352,861 B1 | 3/2002 | Copeland et al. |
| 6,395,558 B1 | 5/2002 | Duveneck et al. |
| 6,395,562 B1 | 5/2002 | Hammock et al. |
| 6,397,150 B1 | 5/2002 | Izmailov |
| 6,399,365 B2 | 6/2002 | Besemer et al. |
| 6,469,785 B1 | 10/2002 | Duveneck et al. |
| 6,471,916 B1 | 10/2002 | Noblett |
| 6,534,645 B2 | 3/2003 | McMillan |
| 6,540,890 B1 | 4/2003 | Bhuller et al. |
| 2002/0031836 A1 * | 3/2002 | Feldstein .................... 436/180 |

* cited by examiner

PORTABLE BIOSENSOR APPARATUS WITH CONTROLLED FLOW

BACKGROUND OF THE INVENTION

1. Field of the Invention

The present invention relates to the field of biosensors. More particularly the present invention relates to methods, compositions and apparatus for a compact, portable, automated biosensor that can detect a wide variety of analytes. Movement of fluids through the biosensor may be controlled to increase the sensitivity and efficiency of analyte detection.

2. Description of Related Art

A need exists for a portable, reliable and sensitive biosensor capable of detecting a wide variety of analytes. Preferably, such a biosensor should be simple to use and sturdy enough for field use under a broad range of environmental conditions. Presently available biosensors are too bulky and fragile for field use, or are not sensitive enough to detect a variety of analytes from environmental or other field samples.

A biosensor is an apparatus that uses specific and/or selective binding interactions with one or more biomolecules ("ligands"), such as peptides, proteins, enzymes, antibodies, receptors, nucleic acids, aptamers, etc. to detect one or more target molecules ("analytes"). Binding of the target molecule to the ligand results in a signal that can be used to detect or quantify the analyte present in a sample. A wide variety of biosensors of different design are known. Typically, these are designed for use in clinical or research laboratories and tend to be very bulky and relatively fragile. For example, U.S. Pat. No. 6,258,606 discloses a multiplexed active biologic electrode array, allowing a variety of protein or nucleic acid biomolecules to be attached to specific locations on an integrated circuit chip. The biomolecules are exposed to samples and binding of various analytes to specific locations on the chip may be detected, for example, by fluorescence spectroscopy. In its commercial form, the biosensor is too bulky and fragile for use under field conditions.

U.S. Pat. No. 6,277,627 discloses a glucose biosensor comprising a genetically engineered glucose binding protein. The binding protein is modified to allow introduction of environmentally sensitive reporter groups. The biosensor is limited to detection of glucose or its close structural analogs and is not suited for detecting a wide variety of analytes.

U.S. Pat. No. 6,294,392 discloses a flow-through microchannel (capillary) biosensor that is said to be suitable for the detection of multiple different analytes in a sample by binding to complementary biomolecules immobilized on the wall of the microchannel. Following initial binding, immobilized complexes are denatured and flow past a downstream detector. The use of microchannels with small cross-sectional diameters would result in frequent clogging of the apparatus unless samples are first processed to remove particulate contaminants. The biosensor is not usable with relatively unprocessed samples that could clog the microchannels.

U.S. Pat. No. 6,171,238 discloses a portable hand-held biosensor device for examination of whole blood, urine and other biological liquids. The system contains a single measuring electrode that can be covered by a biodiaphragm, limiting detection to single analytes at a time. It is not capable of analyzing multiple samples for the presence of multiple analytes simultaneously.

U.S. Pat. No. 6,192,168 discloses a multimode waveguide device and fluidics cube apparatus that may be used as a biosensor. The waveguide may be attached to different biomolecules for detecting various analytes and may contain multiple channels for processing more than one sample at a time. The manufacturing process is complex, involving the machining of multiple layers before assembly into a fluidics cube. The use of a patterned reflective coating on the waveguide increases the cost and complexity of manufacture and may be limiting for the types of chemistry used to bind molecules to the waveguide surface. Non-turbulent fluid flow through the sample channels, the absence of optimized biomolecule attachment sites, and the lack of fixed internal standards result in decreased sensitivity and efficiency of detection. The use of a bezel and gasket to seal the waveguide to the fluidics cube may result in deformation of channels or damage to the waveguide due to improper tightening.

There is a need for portable biosensors that operate reliably with environmental and clinical samples, with minimal sample preparation required before analysis. Such a biosensor should be automated for simple field use and should be sufficiently compact and sturdy to function reliably while subject to jostling, shaking, and extremes of temperature and humidity that may occur in the field. Preferably, the biosensor is capable of analyzing multiple samples for the presence of multiple analytes simultaneously.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

Figure 1:
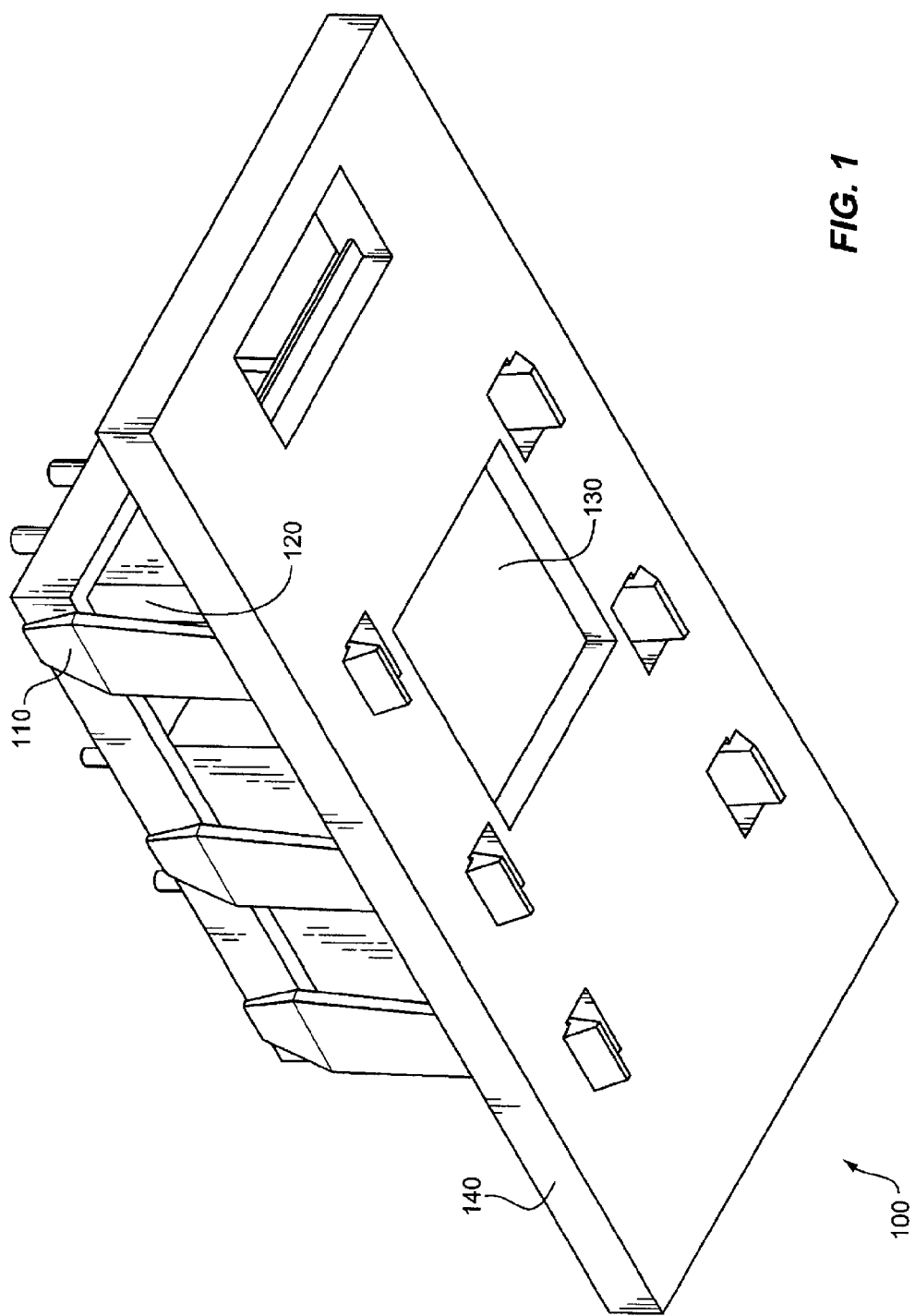
FIG. 1 illustrates an exemplary embodiment of certain aspects of the biosensor, showing a representative fluidics cube attached to a stage.

As used herein, "a" or "an" may mean one or more than one of an item.

As used herein, the terms "analyte," "target" and "target analyte" mean any compound, molecule or aggregate of interest for detection using the biosensor. Non-limiting examples of analytes include a protein, peptide, carbohydrate, polysaccharide, glycoprotein, lipid, hormone, growth factor, cytokine, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal or any other molecule or atom, without limitation as to size. "Analytes" are not limited to single molecules or atoms, but may also comprise complex aggregates, such as a virus, bacterium, Salmonella, Streptococcus, Legionella, E. coli, Giardia, Cryptosporidium, Rickettsia, spore, mold, yeast, algae, amoebae, dinoflagellate, unicellular organism, pathogen or cell. In certain embodiments, cells exhibiting a particular characteristic or disease state, such as a cancer cell, may be target analytes. Virtually any chemical or biological compound, molecule or aggregate could be a target analyte.

As used herein, a "binding moiety" is a molecule or aggregate that has binding affinity for one or more target analytes. The term "binding moiety" is synonymous with the terms "biomolecule" or "ligand" as used herein. Within the scope of the present invention virtually any molecule or aggregate that has a binding affinity for some target analyte of interest may be a "binding moiety." In preferred embodiments, the "binding moiety" is an antibody. In other preferred embodiments, the binding moiety is specific for binding to a single target analyte, although in other embodiments the binding moiety may bind to more than one target analyte exhibiting similar structures or binding domains. With respect to antibody binding, it is anticipated that multiple analytes may exhibit similar or identical antigenic epitopes, resulting in potential cross-reactivity of the binding moiety for related analytes.

"Binding" refers to an interaction between a target analyte and a binding moiety, resulting in a sufficiently stable complex so as to permit detection of the analyte;ligand complex. In certain embodiments, binding may also refer to an interaction between a second molecule and a target analyte. For example, in a sandwich ELISA type of detection assay, the binding moiety is an antibody with affinity for an analyte. After binding of analyte to binding moiety, a second molecule, typically a labeled antibody with an affinity for a different epitope of the analyte, is added and the tertiary complex of first antibody:analyte:second labeled antibody is detected. In alternative embodiments, the first binding moiety may have affinity for a target analyte while the second binding moiety has affinity for the first binding moiety. Although detection may involve the use of a second binding moiety with affinity for an analyte, in alternative embodiments the binary complex of binding moiety with analyte may be directly detected. The skilled artisan will be familiar with a variety of techniques by which an analyte:ligand complex may be detected, any of which may be utilized within the scope of the present invention.

The terms "detection" and "detecting" are used herein to refer to an assay or procedure that is indicative of the presence of one or more specific analytes in a sample, or that predicts a disease state or a medical or environmental condition associated with the presence of one or more specific analytes in a sample. It will be appreciated by those of skill in the art that all assays exhibit a certain level of false positives and false negatives. Even where a positive result in an assay is not invariably associated with the presence of a target analyte, the result is of use as it indicates the need for more careful monitoring of an individual, a population, or an environmental site. An assay is diagnostic of a disease state or a medical or environmental condition when the assay results show a statistically significant association or correlation with the ultimate manifestation of the disease or condition.

Fluidics Cube

Although in preferred embodiments the biosensor is portable and designed for field use, the skilled artisan will realize that the present invention is not limited to portable biosensors. In certain embodiments the biosensor may be designed for use in a clinical or laboratory setting.

In certain embodiments, the biosensor may incorporate a fluidics cube for storage of samples, reagents and buffers and automated analysis of samples for the presence of analytes. An exemplary embodiment of the fluidics cube portion of the portable biosensor apparatus is illustrated in FIG. 1. The skilled artisan will realize that various modifications may be made to individual components of the fluidics cube or to the complete assembly within the scope of the present invention.

FIG. 1 illustrates an embodiment of the fluidics cube portion of the portable biosensor apparatus, comprising a vent cap 10, a cube body 120, a waveguide 130 and a stage 140. The vent cap 110 overlays the cube body 120 and waveguide 130 and attaches to the stage 140. Although not seen in FIG. 1, a vent cap isolator (FIG. 3, 340) is interposed between the cube body 120 and the vent cap 110. The vent cap isolator 340 provides a liquid seal for the fluid filled reservoirs present in the cube body 120, preventing leakage of fluids out of the fluidics cube as well as any cross-contamination between different fluid filled reservoirs. This is an advantage for the design of a fluid filled portable biosensor apparatus to be carried in the field, where it may potentially be tilted, inverted, dropped, accidentally immersed in water or other liquids, etc. The vent cap isolator also acts in part to seal the reservoirs, channels and other compartments of the fluidics cube from connection to the external atmosphere.

In the embodiment shown in FIG. 1, the vent cap 10 attaches to the stage 140, holding the components of the fluidics cube together. The attachment mechanism is shown for illustrative purposes only as comprising legs extending from the lower portion of the vent cap 110, designed to operably connect with corresponding slots in the stage 140 through pawls (FIG. 2, 270) located at the ends of the legs. In certain embodiments, such an attachment mechanism is preferred in that it allows the fluidics cube to be rapidly disassembled and reassembled, for example for cleaning the fluidics cube, loading fluids into the various reservoirs or for attaching a new waveguide 130. The skilled artisan will realize that the present invention is not limited to the preferred embodiment and that any mechanism that allows the assembly of the components of the fluidics cube into a modular unit is contemplated within the scope of the invention. Such attachment mechanisms are well known in the art and include, without limitation, screws, bolts, clamps, hooks, nails, pins, latches, locks, lugs, pins, rivets and glues or adhesives. In preferred embodiments, the attachment mechanism is designed for rapid assembly and disassembly of the fluidics cube.

Figure 2:
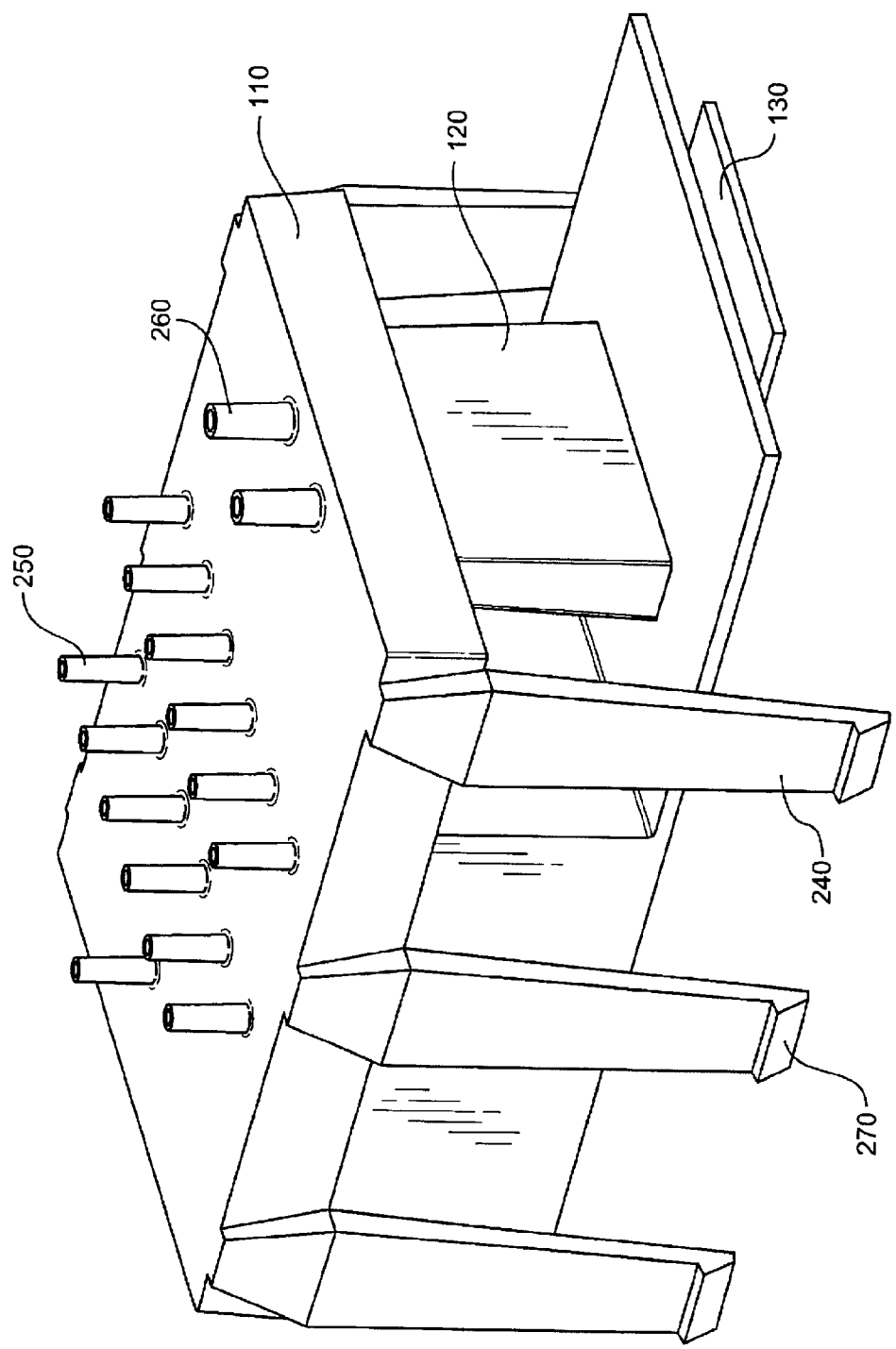
FIG. 2 illustrates a side view of the fluidics cube of FIG. 1, without the attached stage.

FIG. 2 illustrates a side view of the fluidics cube shown in FIG. 1, minus the stage. The components shown FIG. 2 comprise the vent cap 110, cube body 120 and waveguide 130. The vent cap isolator (FIG. 3, 340) is not seen in this view. FIG. 2 more clearly shows a representative design of the legs 240 that operably connect to corresponding slots in the stage (FIG. 1, 140). As shown in FIG. 2, in preferred embodiments the waveguide 130 extends beyond the edge of the cube body 120, where it may more easily be interfaced with a source of excitatory light and/or a detector to detect signals from binding moieties attached to analytes. The upper surface of the vent cap 110 shows a multiplicity of ports 250. Certain of the ports 250 are designed to allow attachment of valves that control the movement of fluids through the various compartments of the fluidics cube during operation. In preferred embodiments, the valves are X-valves from Pneutronics (Hollis, N.H.), although it is contemplated that any valves could be used in the practice of the invention. In their closed position, the valves seal the ports from the atmosphere and prevent the movement of liquids in the various reservoirs, channels and other fluid compartments of the fluidics cube. When in the open configuration, the valves allow the movement of liquids in response to a pressure differential. The pressure differential may be exerted by the application of a positive pressure or a negative pressure.

In certain embodiments, the ports 250 may also be used to load liquids into the underlying reservoirs in the cube body 120, for example by inserting syringes through the ports 250 and the vent cap isolator 340 into the reservoirs. However, in alternative embodiments the reservoirs are loaded with fluids when the fluidics cube is partially disassembled and the vent cap isolator 340 is separated from the cube body 120.

In certain embodiments, the ports 250 may be connected through valves to a positive pressure source, such as an air pump, compressor or a compressed air or gas cylinder. Upon opening the valves, the positive pressure forces air or gas through the ports, displacing liquid from the underlying fluid reservoirs. The liquid flows through the sample channels and eventually exits the fluidics cube through exit ports 260. In this exemplary embodiment, there are two exit ports 260 located on the right side of the vent cap 110 in FIG. 2. Where positive pressure is used, the exit ports may be directly connected, for example, to a waste container. In other embodiments, valves may be interposed between the exit ports 260 and any downstream containers. Alternatively, Luer locks or other valves may be placed in the body of the vent cap to allow manual opening and closing of the exit ports. Such an arrangement may be advantageous to prevent inadvertent contamination of the sample channels when loading the fluid reservoirs.

In alternative embodiments the exit ports 260 may connect to one or more negative pressure sources. In this case, opening the valves attached to the ports 250 allows air to enter the fluid reservoirs and the movement of fluids out of reservoirs, through the sample channels and out the exit ports. As discussed above, the exit ports 260 may contain additional valves to allow further control of fluid movement.

Figure 3:
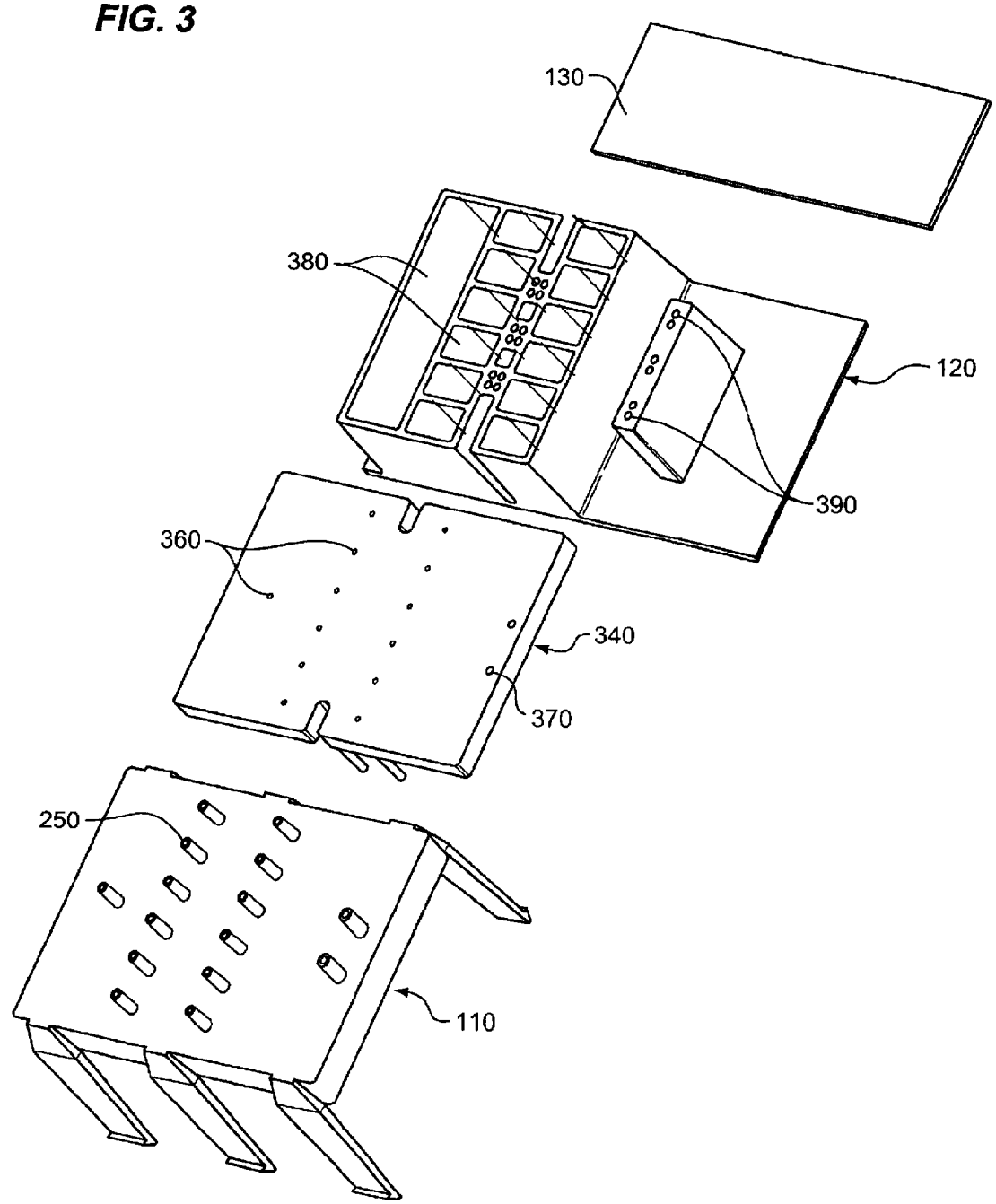
FIG. 3 illustrates the individual components of the fluidics cube shown in FIG. 2, as viewed from their upper surfaces.

FIG. 3 shows the disassembled components of the fluidics cube, comprising the vent cap 110, vent cap isolator 340, cube body 120 and waveguide 130. The stage (FIG. 1) is not shown in FIG. 3. The components are shown from the perspective of their upper surfaces. In comparison to an unfolded view of the vent cap isolator (FIG. 7), the vent cap isolator 340 is shown in FIG. 3 in its folded configuration.

It is apparent that the ports 250 and exit ports 260 in the vent cap 110 are continuous with corresponding air holes 360 or fluid holes 370 that extend through the vent cap isolator 340 and allow access of air to the underlying reservoirs 380 or egress of fluids from the fluid outlet holes 390 of the cube body 120. A series of fluid outlet holes 390 is shown to the right side of the cube body 120, one for each sample channel (FIG. 4).

During operation of the portable biosensor, the reservoirs 380 will normally be filled with buffer, reagents and samples. A negative pressure source applies a partial vacuum to the exit ports 260, or a positive pressure source applies elevated air pressure to the ports 250. When the valves attached to the ports 250 on the vent cap are in a closed position, fluid is prevented from exiting the reservoirs by the tight air seal between the vent cap isolater 340 and the cube body 120. When one or more valves are open, air flows through the ports 250 and replaces the fluids exiting the reservoirs 380, allowing the fluids to pass through the sample channels and eventually to exit the fluidics cube through the exit ports 260.

Figure 4:
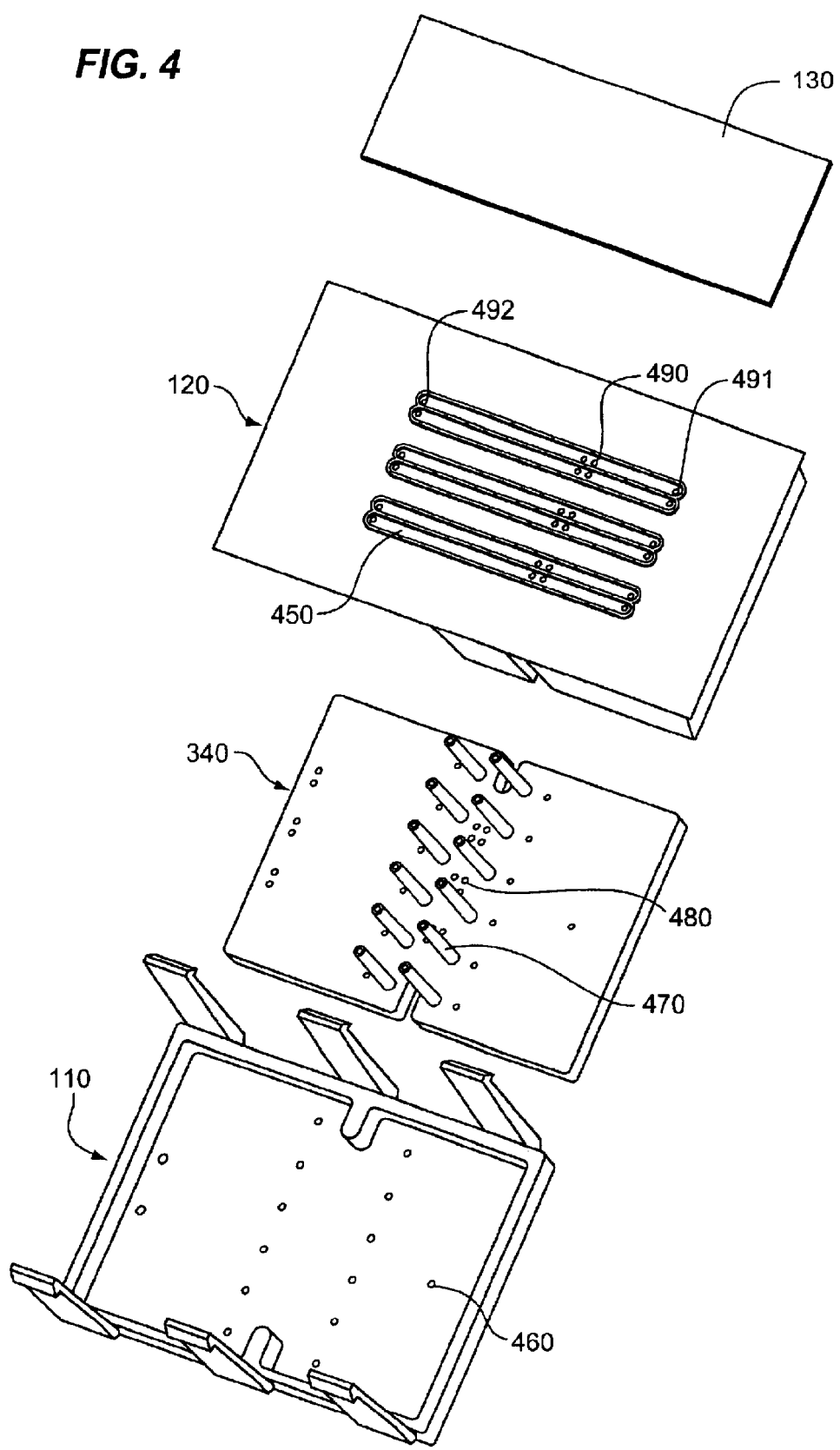
FIG. 4 illustrates the same fluidics cube components, as viewed from their lower surfaces.

FIG. 4 shows the same components as FIG. 3 from the perspective of their lower surfaces. The holes 460 in the vent cap 110 are continuous with the ports 250 or exit ports 260 in the upper surface of the vent cap 110. The lower surface of the vent cap isolator 340 exhibits a series of fluid intake tubes 470, one for each sample and reagent reservoir (FIG. 5) in the cube body 120. When the air valve associated with a sample reservoir is open, fluid flows through the corresponding intake tube 470 through passages within the body of the vent cap isolator 340 and into one of the six sample channels 450 on the lower surface of the cube body 120. Liquids are contained within the sample channels 450 between the lower surface of the cube body 120 and the upper surface of the waveguide 130.

Three sets of four fluid openings 480 each are apparent in the middle of the vent cap isolator 340. Each of these fluid openings 480 is connected through passages within the body of the vent cap isolator 340 to one of the fluid intake tubes 470. Thus, fluid passes from a sample or reagent reservoir up through a fluid intake tube 470 and out of the fluid openings 480. The fluid openings 480 in the vent cap isolator 340 are continuous with a corresponding set of fluid passages in the cube body 120. The sample or reagent enters the sample channels 450 through a corresponding set of entrance holes 490 in the lower surface of the cube body 120. Each sample channel 450 is connected at one end to the buffer reservoir (FIG. 5) through a buffer hole 491 and at the other end to a fluid outlet hole (FIG. 3, 390) through a fluid exit hole 492.

The analysis of samples occurs within the six sample channels 450 on the bottom of the cube body 120. Prior to analysis, various binding moieties are attached to the upper surface of the waveguide 130. The binding moieties are applied only to the portions of the waveguide 130 that are covered by the sample channels 450 on the bottom surface of the cube body 120. After attachment and washing to remove any unattached binding moieties, samples suspected of containing analytes are exposed to one or more of the sample channels 450. Where analytes are present, they bind to the binding moiety. Unbound contaminants are removed by additional washing and bound analytes are detected as described below.

In certain embodiments, the waveguide 130 is discarded after each sample analysis and a fresh waveguide 130 is attached to the lower surface of the cube body 120. It is anticipated that waveguides may either be pre-attached to binding moieties or that binding moieties may be attached to the waveguide prior to each analysis.

Figure 5:
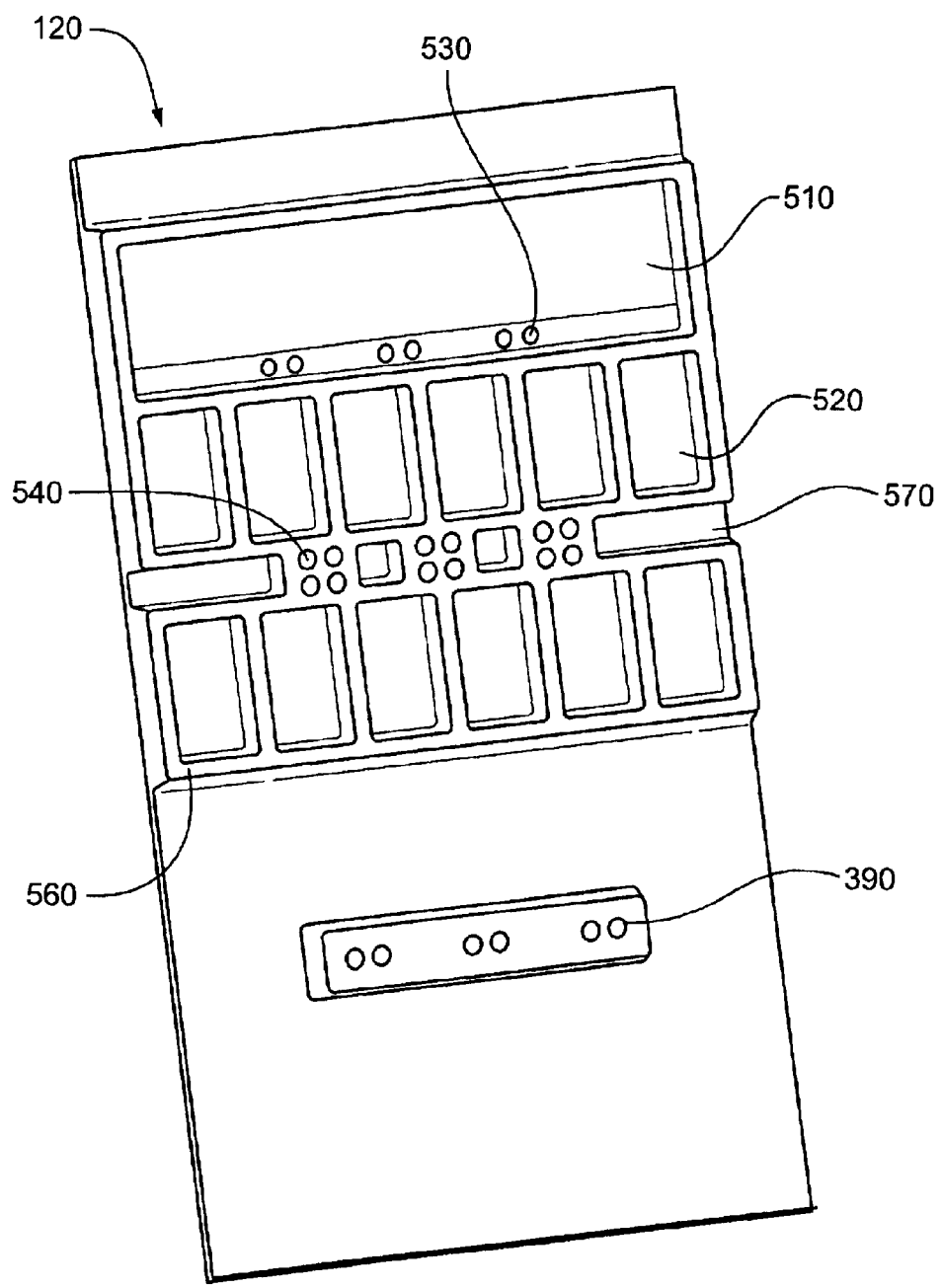
FIG. 5 shows an expanded view of the cube body of the fluidics cube, as viewed from its upper surface.

FIG. 5 shows an enlarged view of the upper surface of the cube body 120. A large buffer reservoir 510 is present at one end of the cube body 120. Six buffer entrance holes 530 are located at the bottom of the buffer reservoir 510. When the air valve associated with the buffer reservoir is open, buffer flows from the buffer reservoir 510 through the buffer entrance holes 530 and through each of the sample channels 450, entering the sample channel 450 through buffer hole 491 and exiting through fluid exit hole 492.

Twelve sample and reagent reservoirs 520 are shown in FIG. 5. Two sample and reagent reservoirs 520 are connected to each sample channel 450. Movement of fluid out of each sample and reagent reservoir 520 is controlled by opening a corresponding valve and applying negative pressure to the exit ports 260 or positive pressure to the ports 250. Fluid moves out of the sample and reagent reservoir 520 up the fluid intake tube 470, through passages in the vent cap isolator 340 and out of the fluid openings 480. The fluid openings 480 in the vent cap isolator 340 are aligned with a corresponding set of sample and reagent entrance ports 540 that connect to the sample channels 450 through entrance holes 490. Fluid outlet holes 390 are continuous with fluid exit holes 492. The upper surface of the cube body 120 composes a top sealing surface 560 that forms an air and liquid tight seal when opposed to the lower surface of the vent cap isolator 340. Two tabs 570 allow proper alignment of the cube body 120 with the vent cap isolator 340.

Figure 6:
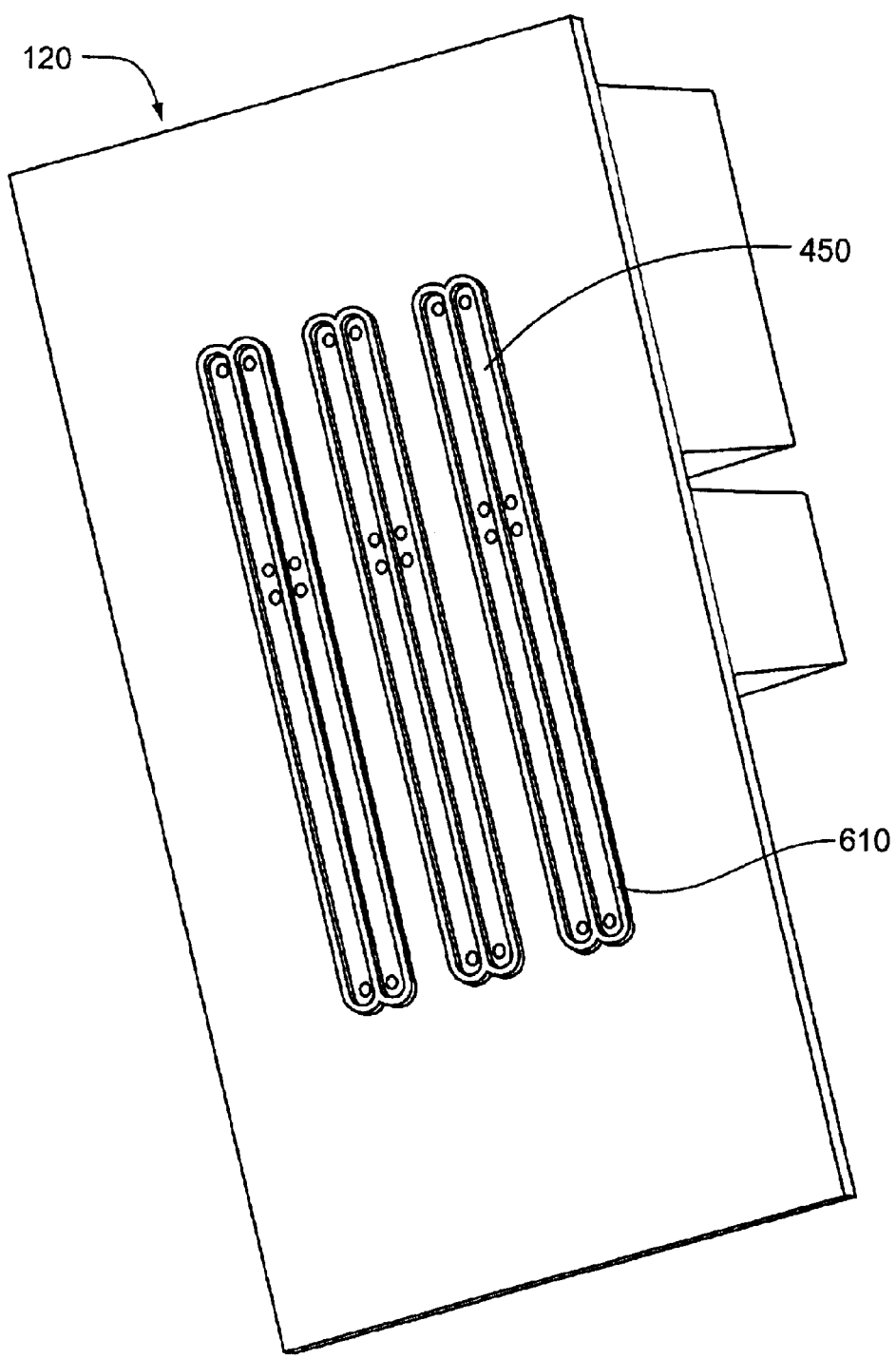
FIG. 6 shows the cube body as viewed from its lower surface.

FIG. 6 shows an enlarged view of the lower surface of the cube body 120. The six sample channels 450 are shown. The lower surface of the cube body composes a waveguide sealing surface 610 that forms an air and liquid tight seal when opposed to the upper surface of the waveguide 130.

Figure 7:
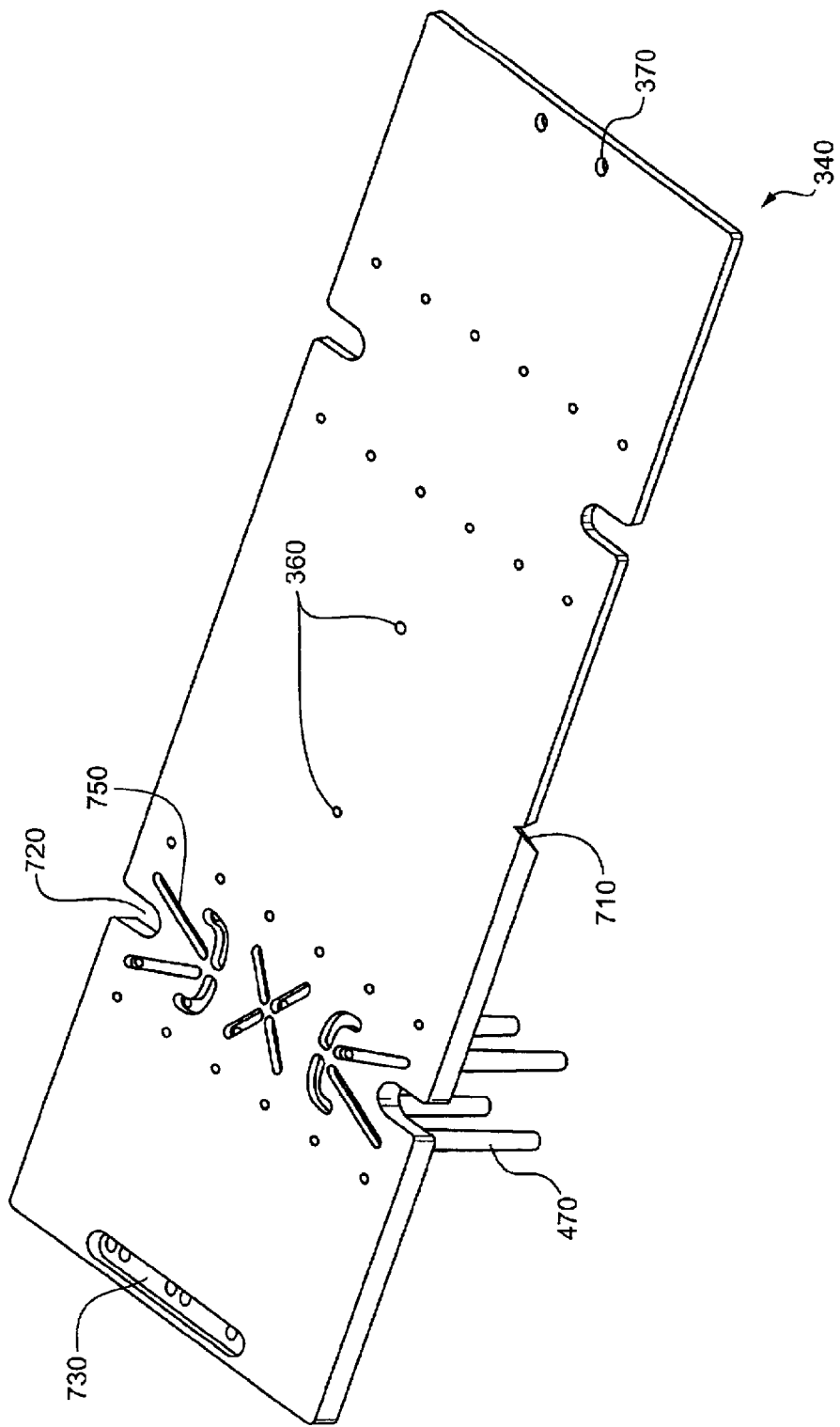
FIG. 7 shows an exemplary embodiment of a vent cap isolater in an unfolded configuration.

FIG. 7 shows an enlarged view of the vent cap isolator 340 in an unfolded configuration. Two hinge points 710 allow the opposite halves of the vent cap isolator 340 to be folded together. The alignment feature 720 consists of four slots that align with the tabs 570 on the upper surface of the cube body 120. An exit port combiner 730 is located at one edge of the vent cap isolator 340. Fluid exiting the sample channels 450 passes through fluid exit holes 492, out of the fluid outlet holes 390 and into the exit port combiner 730. The fluid from the various sample channels 450 is mixed together in the exit port combiner 730 and exits the vent cap isolator 340 through fluid holes 370. Fluid holes 370 are continuous with exit ports 260.

In certain embodiments, the two exit ports 260 both connect to a negative pressure source. In various embodiments, a single negative pressure source or two different negative pressure sources may be used. In alternative embodiments, only one port 260 is attached to a negative pressure source. The other exit port 260 may be attached to a valve. When the valve is open, air flows through one exit port 260, through the other exit port 260 and to the negative pressure source, relieving negative pressure from the rest of the fluidics cube. In alternative embodiments, one or more valves may be incorporated directly into the vent cap 10 instead of being attached to an exit port 260.

FIG. 7 also shows fluid passages 750 in the body of the vent cap isolator 340. The fluid passages 750 connect the fluid intake tubes 470 to fluid openings 480. When the fluidics cube is assembled together, fluid openings 480 are aligned with sample and reagent entrance ports 540. In its folded configuration, the air holes 360 in the two halves of the vent cap isolator 340 are aligned with each other, allowing movement of air and fluid through the vent cap isolator 340.

Figure 8:
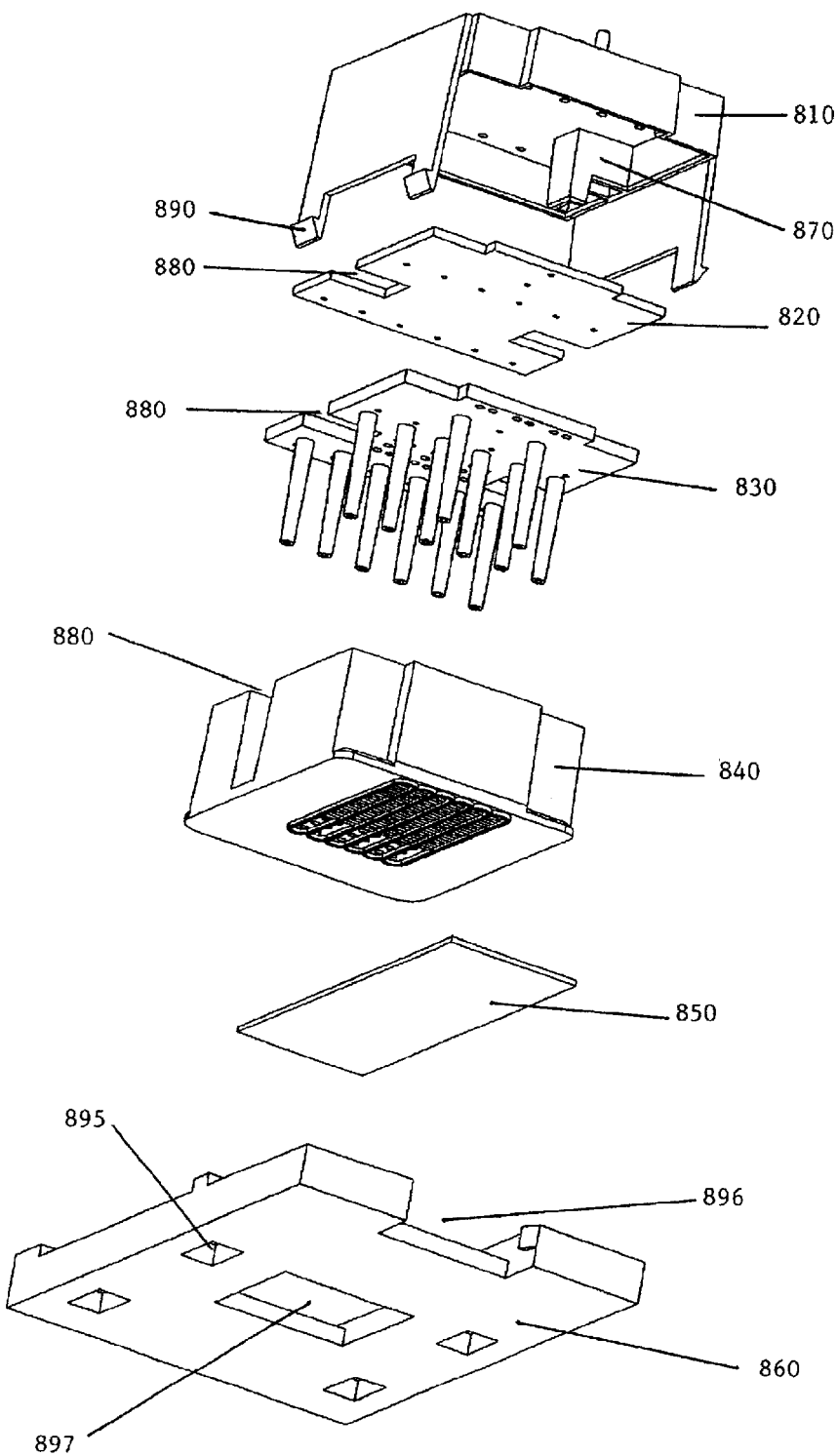
FIG. 8 illustrates a preferred embodiment of certain aspects of the biosensor, showing a preferred fluidics cube design incorporating a waveguide and stage.

A preferred embodiment of the fluidics cube portion of the biosensor is shown in FIGS. 8 to 14. As shown in FIG. 8, the preferred embodiment contains a vent cap 810, cube body 840, waveguide 850 and stage 860. However, the folded vent cap isolator shown in FIG. 3 (340) has been divided into two components—a vent cap isolator 820 and a fluid manifold 830. The vent cap 810 contains two tabs 870 that fit into corresponding alignment slots 880 in the vent cap isolator 820, fluid manifold 830 and cube body 840 and serve to align the fluid and air channels of the fluidics cube. The vent cap 810 contains legs with pawls 890 that fit into attachment slots 895 in the stage 860 and hold the fluidics cube together. As discussed above, any alternative mechanism for attaching the vent cap 810 to the stage 860 is contemplated within the scope of the invention. The stage 860 contains a waveguide slot 896 to align the waveguide 850. A detector aperture 897 allows access for a CMOS or other detector to the waveguide 850.

Figure 9:
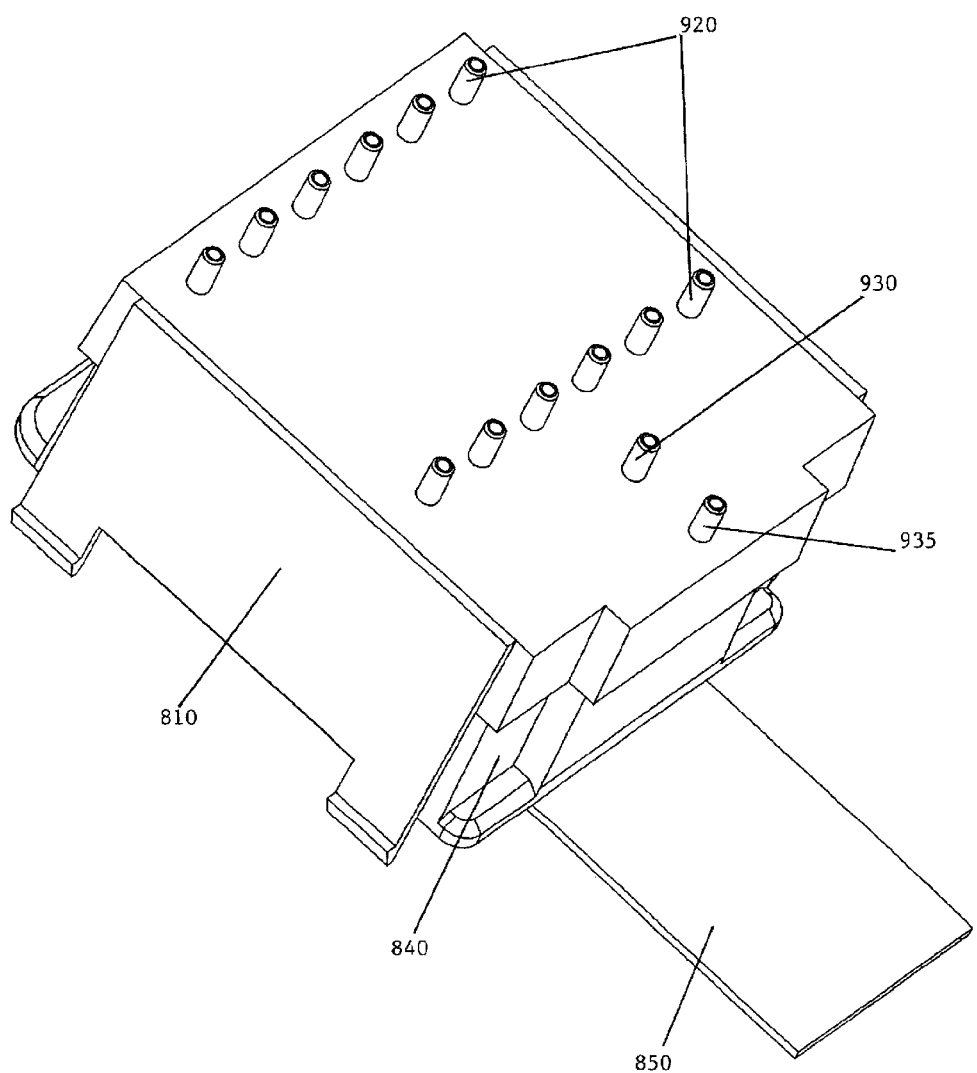
FIG. 9 shows the upper surface of the fluidics cube and waveguide of FIG. 8, without the stage.

FIG. 9 shows an upper view of the fluidics cube without the stage 860. The upper surface of the vent cap 810 contains two sets of ports 920 allowing access to the sample and reagent reservoirs in the cube body 840. A buffer port 930 allows access to the buffer chamber in the cube body 840. A single exit port 935 is provided. As discussed above, valves may be attached to the ports 920, buffer port 930 and exit port 935. In alternative embodiments, one or more valves may be incorporated directly into the vent cap 810. A positive pressure source (air pump, compressor, compressed air cylinder, or equivalent) may be attached to the ports 920 and buffer port 930. Alternatively, a negative pressure source may be attached to the exit port 935. In this embodiment, the waveguide 850 extends substantially past the edge of the cube body 840.

Figure 10:
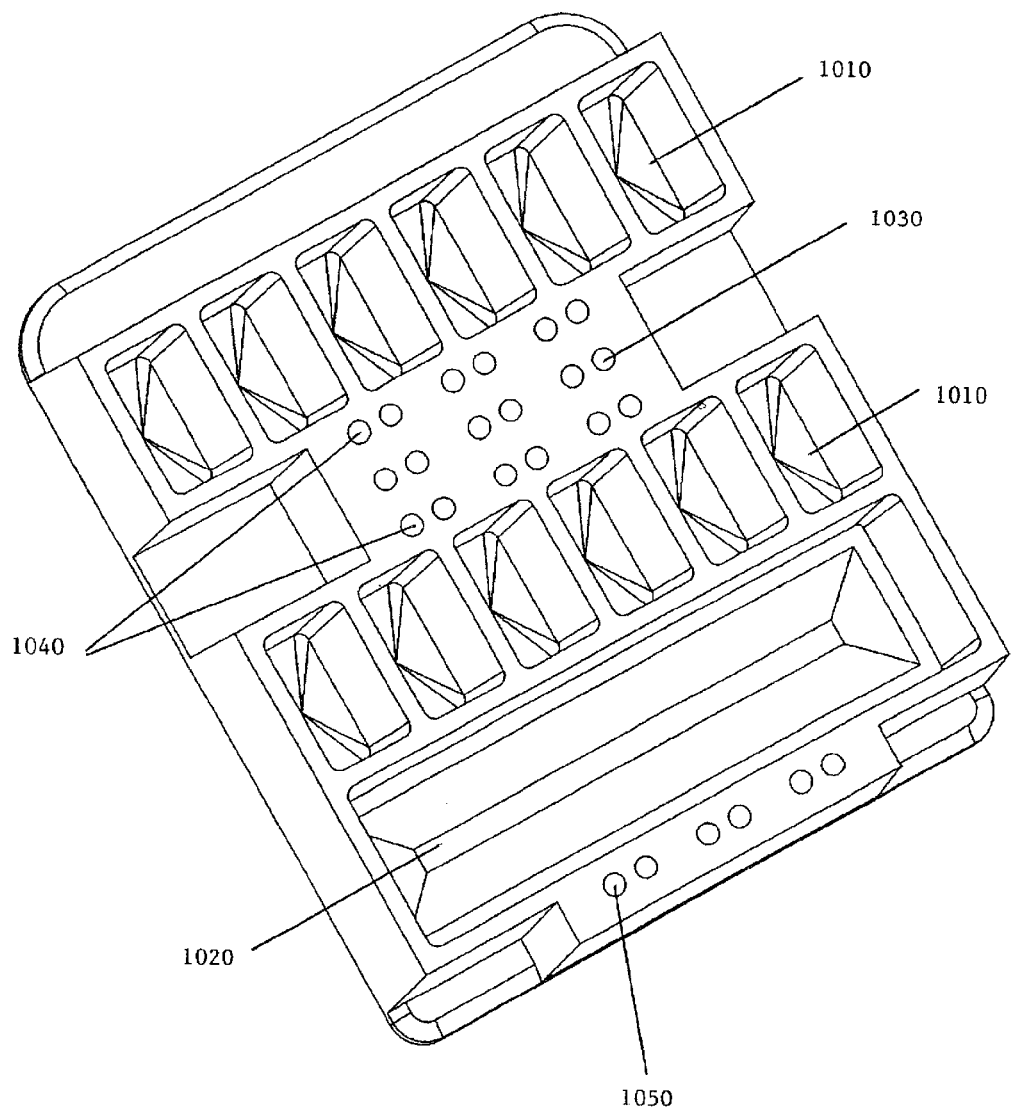
FIG. 10 illustrates a preferred embodiment of the upper surface of the cube body.

The cube body 840 is modified, as shown in FIG. 10. There are still two sets of six sample and reagent reservoirs and a single buffer reservoir 1020. However, the buffer entrance holes have been eliminated. Instead, buffer is provided to the sample channels through six buffer entrance ports 1030. Reagents and samples are still provided to the sample channels through sample and reagent entrance ports 1040. As in the previous embodiment, fluids exit the sample channels through six fluid outlet holes 1050.

Figure 11:
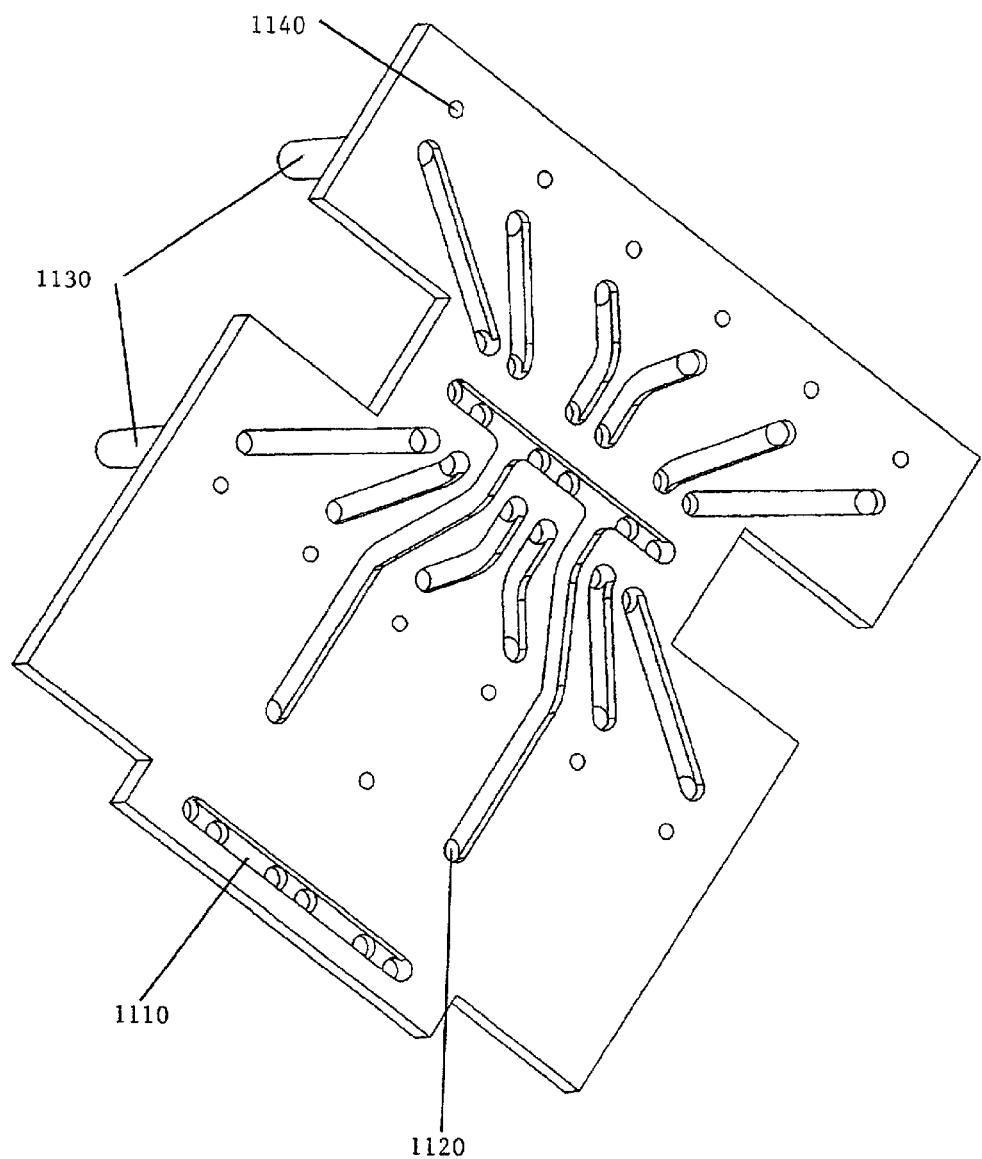
FIG. 11 shows a view of the upper surface of the fluid manifold shown in FIG. 8.

The fluid pathways through the fluid manifold 830 are illustrated in FIG. 11, which shows the upper surface of the fluid manifold 830. An exit port combiner 1110 collects fluid from the six fluid outlet holes 1050 and provides the collected fluid to the exit port 935. Buffer is taken up from the buffer reservoir 1020 through two buffer intake tubes, shown on the lower surface of the fluid manifold 830 in FIG. 8. The buffer enters the fluid manifold through two buffer holes 1120 and is channeled to the buffer entrance ports 1030. Samples and reagents enter the fluid manifold 830 through fluid intake tubes and are channeled to the respective sample and reagent entrance ports 1040. Air holes 1140 connect the ports 920 and buffer port 930 to the underlying reservoirs and allow entry of air or gas to displace reservoir fluids.

Figure 12:
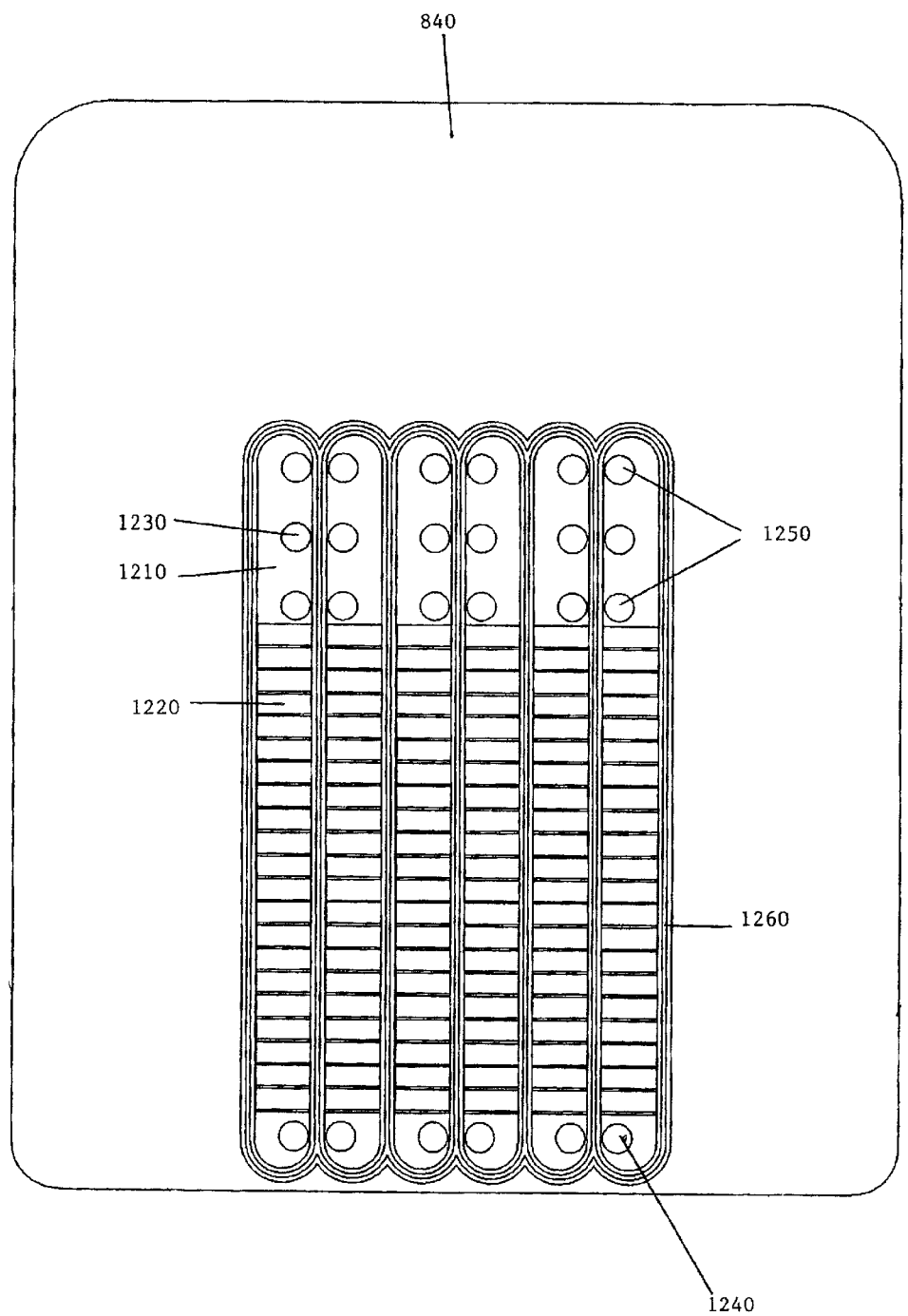
FIG. 12 illustrates the lower surface of the cube body shown in FIG. 8. Sample channels are sealed against the upper surface of the waveguide by a double lip, avoiding the need for a bezel and deformable gasket. An exemplary embodiment of baffles on the upper surface of the sample channels is shown.

FIG. 12 shows the lower surface of the cube body 840. The sample channels 1210 are modified to improve fluid mixing and increase the efficiency and sensitivity of analyte detection. A series of baffles 1220 are located on the upper surface of each sample channel 1210. The baffles divert fluid in a downward direction towards the binding moieties attached to the waveguide 850. This creates a turbulent flow that results in mixing of the fluid contents. The turbulent flow results in increased binding of analytes or reagents to the binding moieties. In alternative embodiments, the baffles are divided in half across the width of each sample channel 1210, with the baffles on the right and left sides of a given sample channel 1210 offset from each other. This arrangement imparts a lateral as well as a downward momentum to fluids flowing through the channel, creating a vortexing action that results in even more efficient fluid mixing and analyte detection. Preferably, the maximum height of the baffles is approximately half the distance from the waveguide 850 surface to the roof of the sample channel 1210. The baffles may extend slightly past the midline of the channel and may have rounded tips. It is also possible to increase mixing by running the fluid flow in a rapid stop-start mode to increase turbulence within the sample channels 1210.

As shown in FIG. 12, buffer enters the sample channels 1210 through buffer holes 1230 and exits the sample channels 1210 while samples and reagents enter the sample channels 1210 through entrance holes 1250. All fluids exit the sample channels 1210 through fluid exit holes 1240. In certain embodiments, the various holes shown in FIG. 12 are 0.063 inches in diameter. FIG. 12 also shows an improved sealing mechanism 1260, comprising a double lip that extends from the lower surface of the cube body 840 and provides a liquid and air-tight seal to the upper surface of the waveguide 850. This mechanism 1260 eliminates the need for using a soft gasket between the cube body 840 and waveguide 850. Such gaskets can deform if improperly tightened and change the sample channel 1210 dimensions, distorting the size and shape of the binding moiety spots which are analyzed. Overtightened gaskets can also result in cracking of the waveguide 850.

Figure 13:
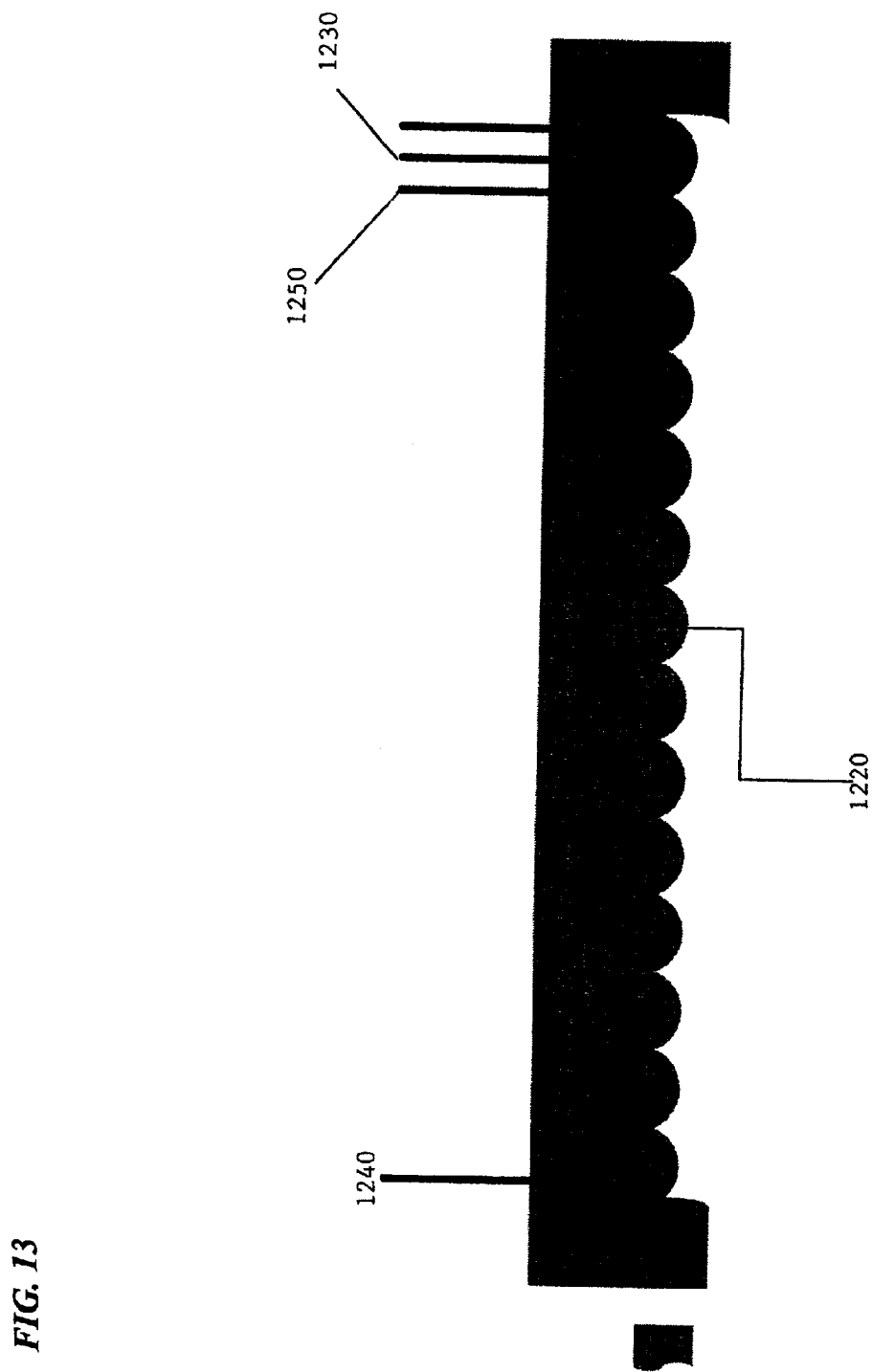
FIG. 13 shows a cross-sectional view of the lower surface of the cube body of FIG. 12. The baffles on the upper surface of the sample channels are more clearly illustrated.

A side view of the baffles 1220 located on the top surface of the sample channels 1210 is illustrated in FIG. 13.

Figure 14:
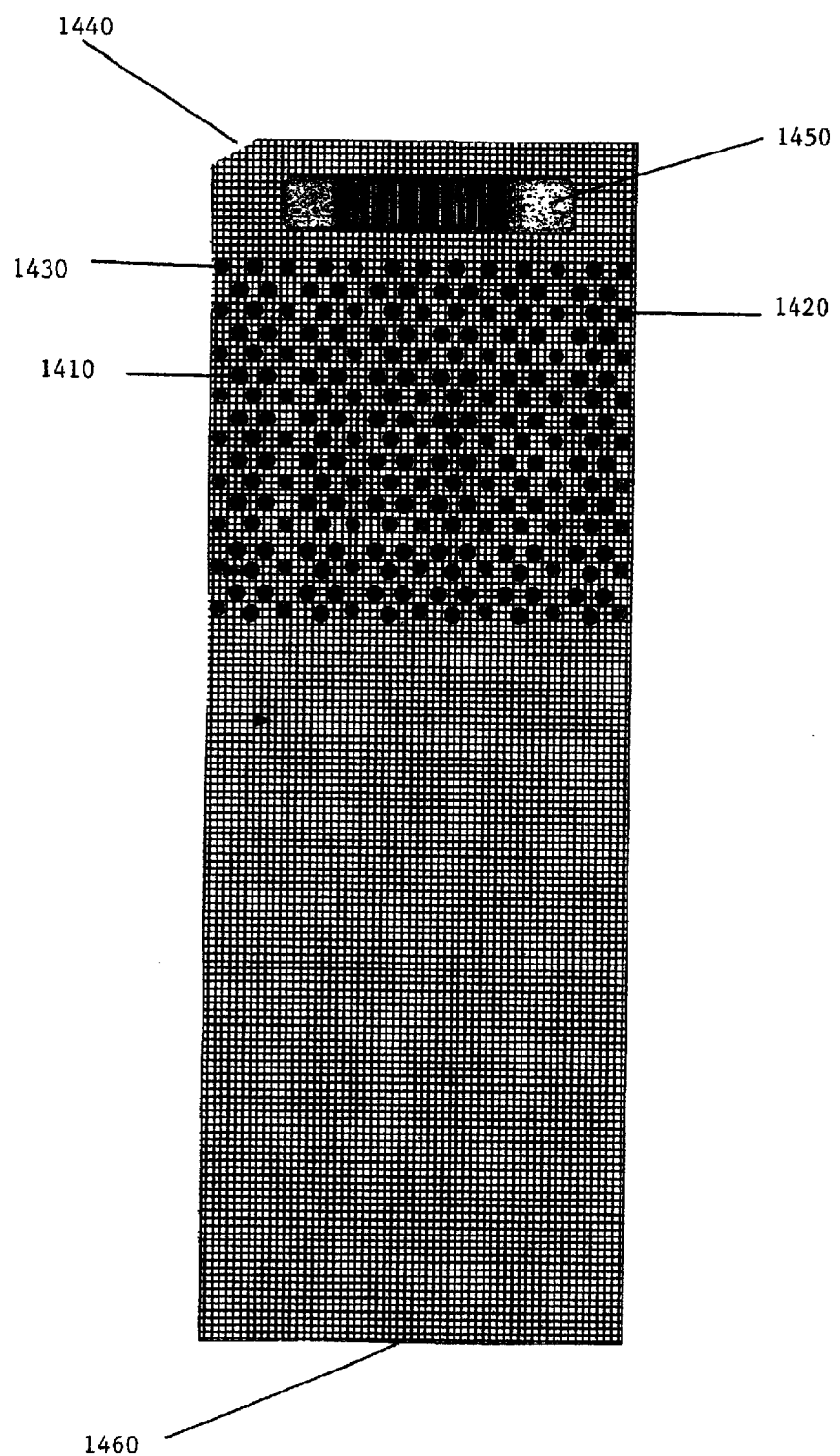
FIG. 14 illustrates a preferred embodiment of the waveguide, with relative locations and configurations of binding moiety attachment sites and calibration spots indicated.

A preferred embodiment of binding moiety spots and calibration spots on a waveguide 850 surface is shown in FIG. 14. The binding moiety and calibration spots are 300 $\mu$m in diameter and the distance between spots is 0.074 inches. A series of binding moiety spots 1410 are arranged in a repeating diamond pattern along the length of each sample channel 1210. The spot pattern may also be described as a hexagon with a spot in the middle, with each spot equidistant from its nearest neighbor. As indicated, in this embodiment a total of 25 binding moiety spots 1410 are contained in each sample channel 1210. In different embodiments, each binding moiety spot 1410 may represent a different binding moiety. The binding moieties attached to each binding moiety spot 1410 may each be specific or selective for a different analyte. Alternatively, different amounts of the same binding moieties may be attached to different binding moiety spots 1410. In another alternative, binding moieties that show different degrees of affinity or that bind to different epitopes on the same analyte may be attached to different binding moiety spots 1410. As each binding moiety spot 1410 may be separately analyzed, the biosensor may be used to assay a single sample for multiple analytes simultaneously. The skilled artisan will realize that the present invention is not limited to the embodiment shown in FIG. 14 and that either greater or lesser numbers of binding moiety spots, of different sizes, conformations and arrangements, may be used in the practice of the invention.

In the preferred embodiment illustrated in FIG. 14, the sample channels 1210 are 0.118 inches wide, with adjacent sample channels 1210 located 0.030 inches apart. The distance from the edge of the waveguide 850 to the center of the first sample channel 1210 is 0.129 inches and the center to center distance between adjacent channels is 0.148 inches. This allows for calibration spots 1420 to be placed along the edges of the waveguide 850 and in between adjacent sample channels 1210. The calibration spots may contain known amounts of a label, for example a fluorophore, to be detected. The amount of label may be identical for each calibration spot or may vary in any desired way. In this way, the detector may be precisely calibrated along the length of each sample channel 1210, allowing the accurate determination of the amount of analyte attached to each binding moiety spot 1410. A unique index spot 1430 may be used to precisely position the calibration spots 1420 and binding moiety spots 1410 on the detector grid. The waveguide 850 may contain a beveled edge 1440 to further facilitate precise positioning of the waveguide 850. The end 1460 of the waveguide 850 exposed to laser excitation is indicated.

In certain embodiments, the waveguides 850 may come with preloaded calibration spots 1420 and binding moiety spots 1410. It is expected that a variety of such preloaded waveguides 850 may be provided, for detection of different analytes or for analysis of different types of samples. In such cases, it is preferred to identify each different type of waveguide 850, for example by use of a bar coding label 1450. In some embodiments, the bar coding label 1450 could be read by the detector simultaneously with data collection. Although a custom waveguide 850 is shown in FIG. 14, it is contemplated that alternative waveguides 850, such as commercially available light microscope slides, could be used in the practice of the invention. An exemplary waveguide 850 is 1.0 inch wide and 3.0 inches long.

The size and arrangement of the binding moiety spots are preferably optimized to maximize the efficiency of analyte detection. The quantitative relationship between surface/volume ratio and adsorption rate disclosed in the reference was used to design the binding moiety pattern disclosed in FIG. 14.

Detection Unit and Waveguide

In certain embodiments, the portable biosensor apparatus comprises one or more detection units operably coupled to the fluidics cube. Optical signals are produced when analytes bind to binding moieties in the sample channels 450, 1210. The signals are transmitted through the waveguide 130, 850 to the detection unit. The detection unit may comprise one or more detectors, such as a spectrometer, monochromator, CCD device, CCD camera, photomultiplier tube, photodiode, avalanche photodiode or any other device known in the art that can detect an optical signal. An optical signal may comprise any form of electromagnetic radiation, emission, or absorption, although in preferred embodiments the optical signal comprises visible light.

In more preferred embodiments, the analyte is associated with a fluorescent tag, as in a sandwich ELISA assay. In this case, the presence of analyte attached to one or more binding moieties is indicated by a fluorescent spot on the surface of the waveguide 130, 850. In other embodiments, the portable biosensor apparatus may comprise a data analysis and storage unit, such as a computer or microprocessor. Suitable devices are well known in the art and the present invention is not limiting as to the type of data analysis and storage unit used. The data analysis and storage unit may be operably coupled to the detection unit, so that optical signals from the fluidics cube are collected, processed and stored. In alternative embodiments, the data analysis and storage unit stores information on each sample collected, including the sample source, geographical location and any other data collected on the sample. The unit may further identify each analyte detected in the sample and store that data as well. In certain embodiments, the portable biosensor apparatus may comprise an interface for downloading data to a remote location, either directly (for example by an incorporated radio transmitter or modem) or indirectly (for example, by downloading to diskette or other storage device or by printing a hard copy).

Figure 15:
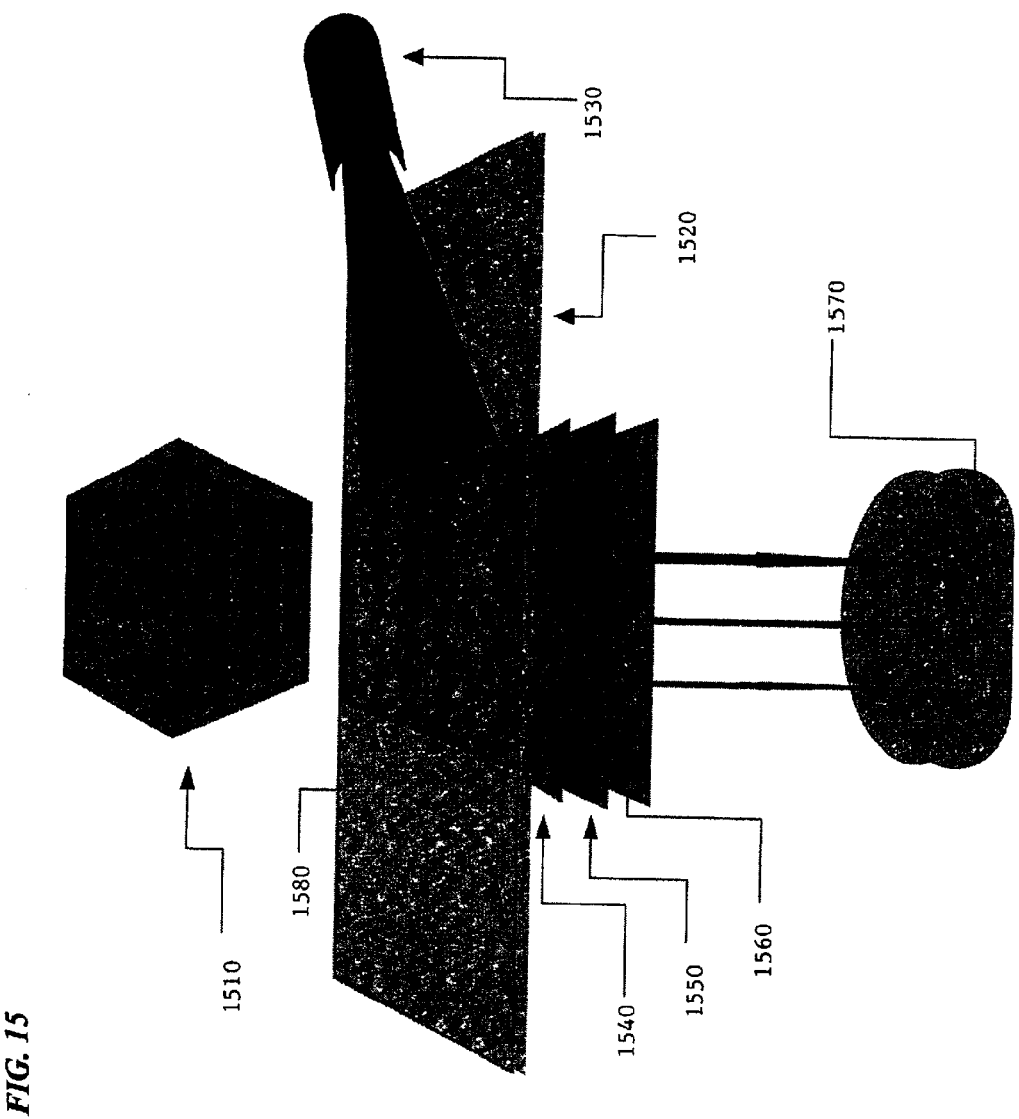
FIG. 15 illustrates a non-limiting example of the relationships between the fluidics cube, waveguide and other components of the biosensor.

An exemplary embodiment of the interface between a fluidics cube, waveguide, detector and excitatory light source is shown in FIG. 15. The fluidics cube 1510 overlays the waveguide 1520. Excitatory light is provided to one edge of the waveguide 1520 by an excitatory light source 1530, such as a diode laser. A non-limiting example of an excitatory light source is a 15 mW LaserMax model LAX 200-635-15 diode laser (LaserMax Inc., Rochester, N.Y.), powered by a wall transformer input (AC 120V 60 Hz 8W) with a direct current output of 5V and 350 ma. Laser input into the waveguide 1520 is accomplished using a line generator that spreads the laser beam into a 1 mm horizontal line. The laser light preferably strikes the edge of the waveguide 1460 at an angle of about 30 degrees. The laser may be turned on and off using controlling software connected via a control interface. Optical signals may be detected through the detector aperture 897 (FIG. 8) using a detector. In certain embodiments, one or more optical components may be interposed between the waveguide 1520 and detector 1570, such as a lens array 1540 to focus optical signals from each spot 1580, a bandpass filter 1550 and a longpass filter 1560 to prevent excitatory light from reaching the detector and to decrease background noise from the waveguide 1520. As indicated, binding moiety spots and calibration spots 1580 may be located on the upper surface of the waveguide 1520. A non-limiting example of a detector 1570 comprises a CMOS camera sensor or equivalent unit, such as a PixeLink model ALM33 CMOS imager (Vitana Corp., Ottawa, Canada).

Figure 16:
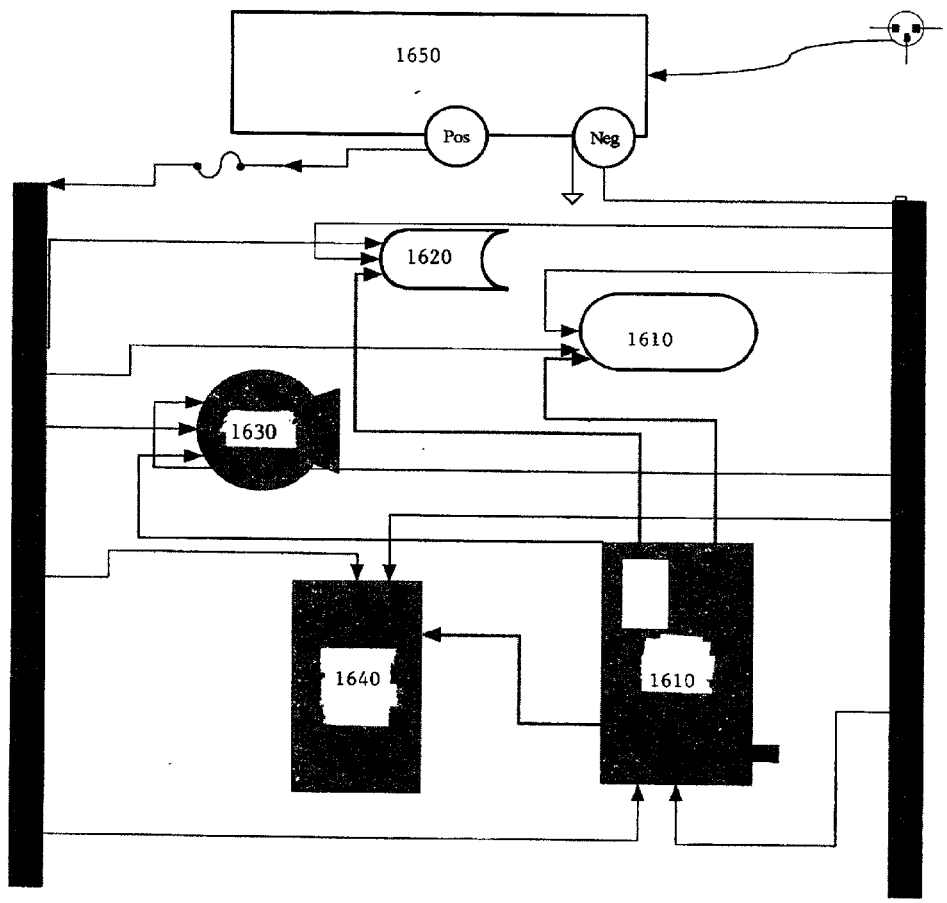
FIG. 16 presents a schematic diagram showing an illustrative embodiment of the electrical connections between various components of the biosensor.

FIG. 16 illustrates a representative schematic diagram showing the electrical connections between different components of the biosensor. In preferred embodiments, a single card controller, such as an ADR2100 serial interface with an ADRTerm strip (Ontrak Control Systems Inc., Sudbury, Ontario), provides automated control for the biosensor. The controller card operates the speed and cycle for a positive or negative pressure source 1610 (such as an InsTech 625/900 peristaltic pump), an excitatory light source 1620, a detector 1630 and one or more valves. The controller card 1610 controls the power on/off operation of the detector 1630, such as a CMOS camera sensor, but image capture and controls are preferably by firewire interface. Although the embodiment shown in FIG. 13 shows a separate valve controller board 1640 (e.g., Pneutronic X-valve controller board), in preferred embodiments the valve control functions are incorporated into the controller card 1610. The power source preferably comprises rechargeable batteries 1650 that may be recharged, supplemented with or replaced by a 14.4 V DC power supply provided by an approximately 120 V wall transformer. In certain embodiments, the system may be interfaced with a computer, such as a Winbook X laptop computer, to provide for data storage and analysis.

In certain embodiments, a CMOS camera with a scan time of about 350 msec is used to detect and quantify optical signals from the waveguide 1520. Because there is an approximately 100 msec delay between the time that the detector begins scanning the front edge of the waveguide 1520 and the time that it begins scanning the back edge, binding moiety spots at the front of the waveguide surface may be overexposed compared to spots at the back, rendering accurate quantitation difficult. To eliminate this effect, it may be preferred in some embodiments to delay activation of the laser excitation beam for 100 msec after initiation of detector scanning. In certain embodiments, multiple exposures of the same waveguide 1520 surface may be preferred. Background optical signals from areas of the waveguide 1520 adjacent to the binding moiety or calibration spots may be subtracted from the signals obtained from the binding moiety or calibration spots.

Figure 17:
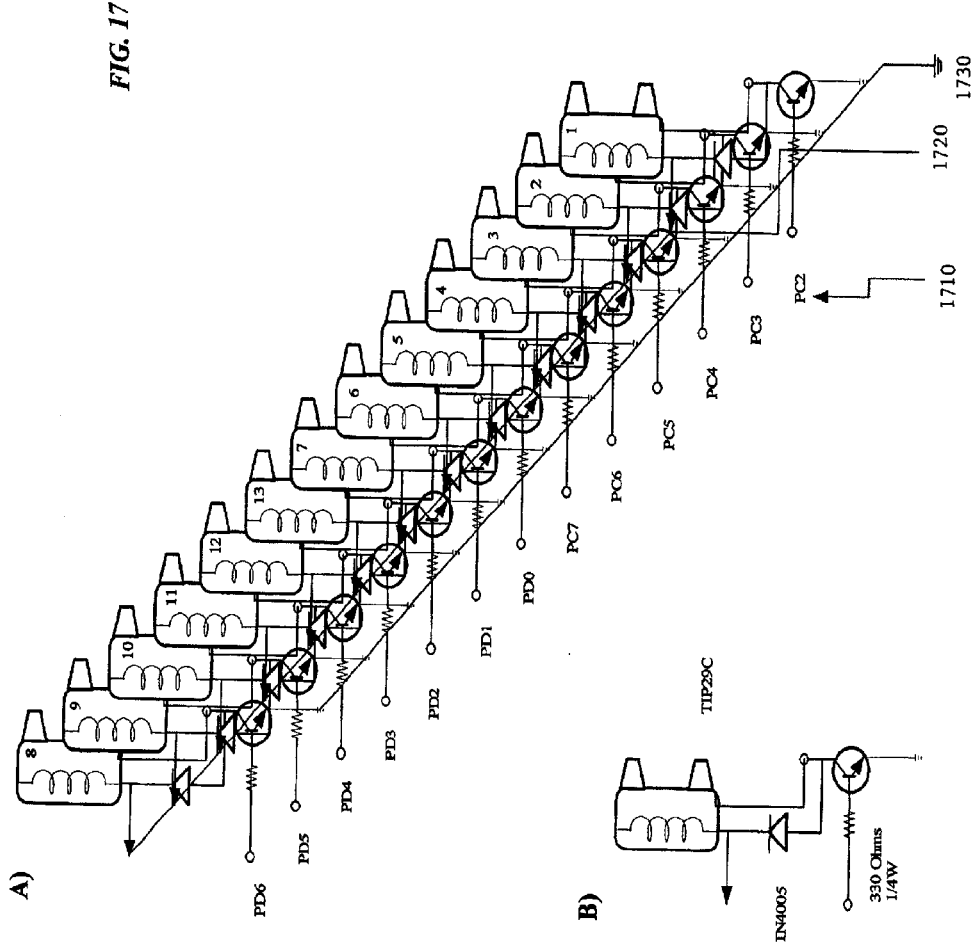
FIG. 17A shows a representative schematic diagram for a circuit board serial interface between the biosensor valve system and the system controller.
FIG. 17B shows a representative schematic diagram for a single valve.

FIG. 17A shows a non-limiting embodiment for a schematic of the serial interface for the valve system employed in the fluidics cube. In this embodiment, 13 valves (for example, Pneutronic X-valves) are attached to the ports 920 and buffer port 930 of the fluidics cube. The valve open or closed positions are solenoid controlled using a 5 V input addressed to each valves from the controller card 1610 or the valve controller board 1640. Each valve is also connected to a 12 V common positive lead 1720 and a common ground 1730. A representative schematic diagram for an individual valve is shown in FIG. 17B.

The skilled artisan will realize that the present invention is not limited to the biosensor configuration disclosed above. It is contemplated that a variety of equivalent components known in the art may be substituted for the disclosed embodiments. Non-limiting alternative embodiments are disclosed in U.S. Pat. Ser. Nos. 5,827,748, 5,858,804, 6,146, 593 and 6,192,168, each incorporated herein by reference in their entirety. The only requirement for the biosensor is that it is capable of detecting binding of an analyte to each binding moiety spot.

In certain embodiments, the binding moieties may be attached directly to the surface of the waveguide 130, 850, 1520, for example by covalent attachment. In other embodiments, binding moieties may be attached to a thin transparent membrane, such as a nylon filter, that can be closely opposed to the waveguide 130, 850, 1520 surface. In preferred embodiments, the waveguide 130, 850, 1520 is a glass slide or the equivalent, although within the scope of the invention it is anticipated that any material that can transmit excitatory and emitted light to and from the binding moiety and calibration spots, the detection unit and the excitatory light source may be used.

Binding Moieties

In various embodiments, the present invention concerns the use of binding moieties for the detection of analytes. Although in preferred embodiments the binding moieties are antibodies, it is contemplated within the scope of the invention that virtually any molecule or aggregate that can bind to a target analyte with sufficient affinity and specificity to allow its detection may be used. Standard procedures for the production of monoclonal or polyclonal antibodies are known (see, e.g., Harlow and Lane, 1988; incorporated herein by reference).

Polyclonal antibodies are prepared by immunizing an animal with an immunogen and collecting antisera from that immunized animal. A wide range of animal species can be used for the production of antisera Typical animals used for production of anti-antisera include, for example, rabbits, mice, rats, hamsters, pigs or horses. Because of the relatively large blood volume of rabbits, a rabbit is a preferred choice for production of polyclonal antibodies.

Antibodies, both polyclonal and monoclonal, may be prepared using conventional immunization techniques, as will be generally known to those of skill in the art. A composition containing antigenic epitopes of an analyte can be used to immunize one or more experimental animals, such as a rabbit or mouse, which will then proceed to produce specific antibodies against the analyte. Polyclonal antisera may be obtained, after allowing time for antibody generation, simply by bleeding the animal and preparing serum samples from the whole blood.

A given composition may vary in its immunogenicity. It is often necessary, therefore, to boost the host immune system, as may be achieved by coupling an immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating an analyte to a carrier protein are well known in the art and include glutaraldehyde, m-maleimidobenzoyl-N-hydroxysuccinimide ester, carbodiimide and bis-biazotized benzidine.

The immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection also may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

Monoclonal antibodies may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified composition comprising an analyte. The immunizing composition is administered in a manner effective to stimulate antibody producing cells. Cells from rodents such as mice and rats are preferred, however, the use of rabbit, sheep or frog cells is also possible.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus (Kohler and Mistein, 1975; 1976), and those using polyethylene glycol (PEG), such as 37% (v/v) PEG, have been described by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, the viable, fused hybrids may be differentiated from the parental, unfused cells by culturing in a selective medium that contains an agent that inhibits cell growth for unfused cells. Exemplary agents are aminopterin, methotrexate, and azaserine. Where aminopterin or methotrexate are used, the medium is supplemented with hypoxanthine and thymidine as a source of nucleotides (HAT medium). Where azaserine is used, the medium is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines also could be cultured in vitro, where the mAbs are naturally secreted into the culture medium from which they can be readily obtained in high concentrations. Monoclonal antibodies produced by either means may be further purified, if desired, using filtration, centrifugation, and various chromatographic methods such as HPLC or affinity chromatography.

Although the methods and compositions disclosed herein allow for the production of novel antibodies against analytes, it is contemplated within the scope of the invention that previously characterized antibodies or commercially available antibodies may be used to bind to and detect any analyte of interest.

Non-antibody binding moieties that may be used within the scope of the present invention include, for example, aptamers (e.g., U.S. Pat. Nos. 5,270,163; 5,567,588; 5,670,637; 5,696,249; and 5,843,653, incorporated herein by reference), peptide libraries (e.g., U.S. Pat. Nos. 5,565,332, 5,596,079, 6,031,071 and 6,068,829, incorporated herein by reference), and various receptor proteins, binding proteins, cell surface proteins, and other non-antibody peptides or proteins known in the art.

Detection of Analytes

A variety of samples may be analyzed by the methods and apparatus of the present invention, including virtually any type of environmental, clinical, veterinary, pathologic or medical sample. In different embodiments, samples may be analyzed after collection without any sample treatment whatsoever. In other embodiments, samples may be processed after collection and before analysis. Samples may be processed in various ways, including without limitation cooling, freezing, heating, homogenization, organic phase extraction, detergent extraction, enzymatic digestion, centrifugation, filtration, ultracentrifugation, ultrafiltration, lyophilization or various well known chromatographic procedures. In certain embodiments, it is anticipated that solid samples may be treated by homogenization and, if necessary, crude filtration, such as filtering the sample through a nylon or other filter with a pore size of approximately 100 $\mu$m or less.

After processing, antibodies or other binding moieties can be used to detect and/or quantify the amounts of analytes in samples through techniques such as ELISA or any other detection methods known in the art. The use of ELISA assays is specifically contemplated. In an exemplary embodiment, antibodies are immobilized on a selected surface, such as a waveguide 130, 850, 1520 surface, that has been incorporated into a sample channel 450, 1210. After washing to remove incompletely adsorbed material, it may be desired to bind or coat the surface with a non-specific material that is known to be antigenically neutral with regard to the test antisera, such as bovine serum albumin (BSA), casein, solutions of powdered milk or detergents such as Tween®. This blocks non-specific adsorption sites on the immobilizing surface and thus reduces the background caused by non-specific binding of antigen onto the surface. Although use of a non-specific blocking agent is preferred, other methods of compensating for non-specific adsorption, such as subtraction of background levels determined from waveguide 130, 850, 1520 surfaces that do not contain bound antibody are known in the art and may be used in the practice of the present invention.

After binding of antibody to the surface, coating with a non-reactive material to reduce background, and washing to remove unbound material, the immobilizing surface is contacted with the sample to be tested in a manner conducive to immune complex (antigenlantibody) formation. Following formation of specific immunocomplexes between the test sample and the bound antibody, and subsequent washing, the occurrence and/or amount of immnunocomplex formation may be determined by subjecting the immunocomplex to a second antibody having affinity for a different epitope of the analyte. Appropriate conditions preferably include diluting the sample with diluents such as BSA, bovine gamma globulin (BGG) or phosphate buffered saline (PBS)/Tween®. These added agents also tend to assist in the reduction of nonspecific background. The antisera is then allowed to incubate. Following incubation, the antiseracontacted surface is washed so as to remove non-immunocomplexed material. A preferred washing procedure includes washing with a solution such as PBS/Tween® or borate buffer.

To provide for detection of bound analyte, the second antibody may have an associated enzyme that will generate a color development upon incubating with an appropriate chromogenic substrate. Thus, for example, one may contact and incubate the second antibody-bound surface with a urease or peroxidase-conjugated anti-IgG for a period of time and under conditions that favor the development of immunocomplex formation. After incubation with the labeled antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

In preferred embodiments, the second antibody may be labeled with one or more fluorescent or luminescent moieties, allowing detection of bound analyte by detection of an optical signal. Specific examples of fluorescent or luminescent labels are well known in the art and are described in more detail below.

In another exemplary embodiment, the preceding format may be altered by first binding the sample to the test section surface. Then, primary antibody is incubated with the bound sample, followed by detection of bound primary antibody using a labeled second antibody with specificity for the primary antibody.

Immunoassays for detecting analytes may be either competitive or noncompetitive. Noncompetitive immunoassays are assays in which the amount of analyte is directly measured, such as the sandwich ELISA described above. In competitive assays, the amount of analyte present in the sample is measured indirectly by measuring the amount of an added (exogenous) analyte displaced (or competed away) from a binding moiety by the analyte present in the sample. In one competitive assay, a known amount of labeled analyte is added to the sample and the sample is then contacted with an antibody that specifically binds to the analyte. The amount of labeled analyte bound to the antibody is inversely proportional to the concentration of unlabeled analyte present in the sample.

In preferred embodiment, the antibody is immobilized on a solid substrate, such as a waveguide 130, 850, 1520. The amount of analyte bound to the antibody may be determined either by measuring the amount of analyte present in an analyte/antibody complex, or alternatively by measuring the amount of remaining uncomplexed analyte, for example by providing labeled analyte or an analog thereof.

A hapten inhibition assay is another preferred competitive assay. In this assay analyte is immobilized on a solid substrate, such as a waveguide 130, 850, 1520. A known amount of antianaltye antibody is added to the sample, and the sample is then contacted with the immobilized analyte. In this case, the amount of antibody bound to the immobilized analyte is inversely proportional to the amount of analyte present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Other assay formats include liposome immunoassays (LIA), which use liposomes designed to bind specific molecules (e.g., antibodies) and release encapsulated reagents or markers. The released chemicals are then detected according to standard techniques (Monroe et al., 1986). The skilled artisan will realize that the immunological methods of use in the practice of the present invention are not limited to those disclosed herein, but may include any immunodetection method known in the art.

Labels

For certain embodiments, it may be desirable to incorporate a label into a binding moiety, analyte, or analog of an analyte. A number of different labels may be used, such as fluorophores, chromophores, radioisotopes, enzymatic tags, antibodies, chemiluminescent, electroluminescent, affinity labels, etc. One of skill in the art will recognize that these and other label moieties not mentioned herein can be used in the practice of the present invention.

Examples of affinity labels include an antibody, an antibody fragment, a receptor protein, a hormone, biotin, DNP, and any polypeptide/protein molecule that binds to an affinity label.

Examples of enzymatic tags include urease, alkaline phosphatase or peroxidase. Colorimetric indicator substrates can be employed with such enzymes to provide a detection means visible to the human eye or spectrophotometrically.

The following fluorophores are contemplated to be useful in practicing the present invention. Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In certain preferred embodiments, it is contemplated that fluorescently labeled beads, such as FluoSpheres (Molecular Probes, Eugene, OR) may be used to fluorescently tag analytes. For example, a second antibody with affinity for the analyte may be covalently or noncovalently attached to a FluoSphere and used in a sandwich ELISA type assay. FluoSpheres have the advantage of providing a more intense fluorescent label, allowing detection of analytes at increased sensitivity. It is contemplated that known quantities of FluoSpheres could also be used to create calibration spots on the waveguide 130, 850, 1520. In certain embodiments, Alexa Fluor 647 is preferred as a fluorescent label. The fluorophore provides a brighter evanescent wave than other available fluorophores and is stable over a broad pH range from 4 to 10.

Cross-Linking Reagents

In preferred embodiments, the binding moieties or analytes of interest may be attached to a surface by covalent or non-covalent interaction. In other preferred embodiments, labels may be attached to binding moieties or to analytes of interest. One means for promoting such attachments involves the use of chemical or photo-activated cross-linking reagents. Such reagents are well known in the art and it is contemplated that any such reagent could be of use in the practice of the claimed invention.

Homobifunctional reagents that carry two identical functional groups are highly efficient in inducing cross-linking. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiolreactive group.

Exemplary methods for cross-linking molecules are disclosed in U.S. Pat. No. 5,603,872 and U.S. Pat. No. 5,401,511, incorporated herein by reference. Various ligands can be covalently bound to surfaces through the cross-linking of amine residues. Amine residues may be introduced onto a surface through the use of aminosilane, for example. Coating with aminosilane provides an active functional residue, a primary amine, on the surface for cross-linking purposes. In another exemplary embodiment, the surface may be coated with streptavidin or avidin with the subsequent attachment of a biotinylated molecule, such as an antibody or analyte. In preferred embodiments, ligands are bound covalently to discrete sites on the surfaces. To form covalent conjugates of ligands and surfaces, various cross-linking reagents have been used, including glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC).

In another non-limiting example, heterobifunctional cross-linking reagents and methods of using the cross-linking reagents are disclosed in U.S. Pat. Ser. No. 5,889,155. The cross-linking reagents combine, for example, a nucleophilic hydrazide residue with an electrophilic maleimide residue, allowing coupling in one example, of aldehydes to free thiols. The cross-linking reagent used can be designed to cross-link various functional groups.

Data Analysis

In certain embodiments, the present invention concerns the use of data analysis for detection of analytes and discrimination from other components of a potentially complex sample mixture. In preferred embodiments where monospecific antibodies are used (e.g., antibodies that will only bind to a single antigen), the data analysis consists simply of whether or not a given analyte is present in the sample and binds to the antibody of interest. The results of such analyses may of course be stored in the data analysis unit, including associated information such as the source of the sample, time of collection, volume of sample analyzed, etc. In more complex situations, cross-reactivity of the various antibodies or other binding moieties against different antigens may be observed. This is particularly likely to occur when the samples to be analyzed contain very complex mixtures of structurally similar antigens. For example, it may be desired to differentiate between the presence of pathogenic organisms, such as bacteria or viruses, and closely related non-pathogenic strains of the same or similar species.

In preferred embodiments, the presence of a target analyte may be indicated by a specific subset of antibodies that are known to bind to that analyte. The presence of the analyte in a sample is indicated by an antigen that binds to that subset of antibodies. In the more complex situation, the presence of analyte in a sample does not result in a unique subset of antibodies binding to the analyte. In this case, more complex methods of data analysis, such as by pattern recognition analysis, may be desired. The skilled artisan will realize that any form of data analysis that is capable of distinguishing between binding of a target analyte versus other antigens in the sample may be of use in the practice of the present invention. Non-limiting examples of pattern recognition methods are disclosed in U.S. Pat. Nos. 4,651,297; 6,117,193; 6,198,847 and 6,210,465, the relevant portions of each of which are incorporated herein by reference.

In general, an array of binding moieties (antibodies) may preferably be arranged as a two-dimensional matrix, wherein a specific antibody is located at a defined position on the array. This can be represented as a set of x,y coordinates, each of which corresponds to a single species of antibody. Where there are multiple copies of the single antibody present at each location, some may bind to an antigen while others may not, depending on the affinity of the antibody for the antigen. Thus, in addition to the x,y coordinates for antibodies that bind to antigen in a sample, there may be an intensity value for each location, representing the number of individual antibody molecules bound to antigen and reflective of the affinity for the antigen—the higher the affinity the more saturated with antigen the location will be. The data to be included in the pattern recognition analysis thus includes the location (x,y coordinate) of each antibody species that binds antigen, as well as the intensity of binding for each location. Including intensity information, it is possible to represent the data as a set of x,y,z values. The patterns of these values for the array may be determined in the presence of a variety of standard antigens, including the target analytes of interest.

The data may be stored in any convenient format, for example in a computer, for comparison to unknown samples. Analysis of the data may be performed by use of pattern recognition, neural network, or other analytical methods well known in the art.

In preferred embodiments, the binding moieties are located in discrete spots as illustrated above. The location of the spots in x,y coordinates is subject to some variability, depending on the precise positioning of the waveguide relative to the detector. For purposes of data analysis, the system may determine the outer bounds of the variability in x,y position and build a square window large enough to capture the optical signal from the entire spot, allowing for positioning variability, but small enough to exclude any signal from adjacent spots. The window is centered on the x,y coordinates of each spot analyzed. Background may be subtracted in the window and the signal corrected to the true spot size before quantifying the signal. Kits All the essential materials and reagents required for the various aspects of the present invention may be assembled together in a kit. When the components of the kit are provided in one or more liquid solutions, the liquid solution preferably is an aqueous solution, with a sterile aqueous solution being particularly preferred.

Such kit components may comprise isolated primary and secondary antibodies with or without a label, reagents for developing and/or detecting a label, standard proteins, buffers, detergents and any other compositions of use in the practice of the claimed invention. Such compositions may be liquid, frozen or lyophilized.

Preferred kits would contain all materials needed for field use of the biosensor. Such materials would preferably be contained in color-coded containers, each color corresponding to a similarly colored reservoir or loading por on the biosensor. In certain embodiments, the materials could be preloaded into syringes or other devices for injection into loading ports. A matching color coding scheme would preferably be used with such injectors, corresponding to colored loading ports.

The components of the kit may be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained. Additionally, instructions for use of the kit components is typically included.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Campbell, In: *Monoclonal Antibody Technology, Laboratory Techniques in Biochemistry and Molecular Biology*, Burden and Von Knippenberg, Eds., Vol. 13:75–83, Elsevier, Amsterdam, 1984.

Gefter et al., *Somatic Cell Genet.*, 3: 231–236, 1977.

Goding, In: Monoclonal Antibodies: *Principles and Practice*, 2d ed., Academic Press, Orlando, Fla., pp. 60–61, and 71–74, 1986.

Harlow and Lane, *Antibodies: A Laboratory Manual*, Cold Spring Harbor Laboratory, Cold Spring Harbor, N.Y., 1988.

Kohler and Milstein, *Nature*, 256:495–497, 1975.

Kohler and Milstein, *Eur. J. Immunol.*, 6: 511–519, 1976.

Monroe et al., *Immunol. Invest.* 15:263–286, 1986

U.S. Pat. No. 4,196,265
U.S. Pat. No. 4,691,297
U.S. Pat. No. 5,270,163
U.S. Pat. No. 5,401,511
U.S. Pat. No. 5,565,332
U.S. Pat. No. 5,567,588
U.S. Pat. No. 5,596,079
U.S. Pat. No. 5,603,872
U.S. Pat. No. 5,670,637
U.S. Pat. No. 5,696,249
U.S. Pat. No. 5,827,748
U.S. Pat. No. 5,843,653
U.S. Pat. No. 5,858,804
U.S. Pat. No. 5,889,155
U.S. Pat. No. 6,031,071
U.S. Pat. No. 6,068,829
U.S. Pat. No. 6,117,193
U.S. Pat. No. 6,146,593
U.S. Pat. No. 6,192,168
U.S. Pat. No. 6,198,847
U.S. Pat. No. 6,210,465

What is claimed is:

1. A biosensor apparatus comprising:
   a) cube body having a top surface and a bottom surface, said bottom surface having one or more sample channels in fluid communication with one or more openings in the top surface, said top surface having one or more fluid reservoirs;
   b) a vent cap having at least two openings;
   c) a vent cap isolator having a top surface, a bottom surface, at least two holes extending between said top and bottom surface, one or more fluid intake tubes extending from the bottom surface and in fluid communication with one or more openings in the bottom surface of the vent cap isolator, said vent cap isolator coupled between the top surface of the cube body and the vent cap such that said at least two holes are in fluid communication with the at least two openings of the vent cap, the one or more fluid intake tubes are in fluid communication with the one or more fluid reservoirs of the cube body and the one or more openings in the bottom surface of the vent cap isolator are in fluid communication with the one or more openings in the top surface of the cube body;
   d) a waveguide coupled to the bottom surface of the cube body; and
   e) a stage attached to the vent cap such that the vent cap isolator, cube body and waveguide are positioned between the stage and vent cap.

2. The apparatus of claim 1, wherein the vent cap isolator provides an air and liquid tight seal for fluid reservoirs in the cube body.

3. The apparatus of claim 1, further comprising one or more valves, wherein said valves are attached to at least one of the openings on the vent cap.

4. The apparatus of claim 1, wherein the vent cap comprises two or more legs designed to operably connect with said stage.

5. The apparatus of claim 1, wherein a seal is formed between said cube body and said waveguide by a double lip on the bottom surface of said cube body.

6. The apparatus of claim 5, wherein said sample channels comprise baffles.

7. The apparatus of claim 1, further comprising a detector to detect emitted light from the waveguide.

8. The apparatus of claim 7, further comprising an excitatory light source to provide excitatory light to the waveguide.

9. The apparatus of claim 8, further comprising one or more optical filters to filter emitted or excitatory light.

10. The apparatus of claim 8, further comprising a power supply and a system controller operably coupled to the detector and excitatory light source.

11. The apparatus of claim 10, further comprising a data analysis and storage unit operably coupled to the detector.

12. The apparatus of claim 1, further comprising a positive pressure source coupled to the vent cap.

13. The apparatus of claim 1, further comprising a negative pressure source coupled to the vent cap.

14. The apparatus of claim 1, further comprising one or more binding moiety spots and one or more calibration spots on the surface of said waveguide.

15. The apparatus of claim 14, wherein said calibration spots comprise fluorescent beads.

16. The apparatus of claim 14, wherein said waveguide is labeled with a bar code.

17. A method of detecting an analyte in a sample comprising:
    a) providing an apparatus according to claim 1;
    b) contacting one or more samples with the one or more sample channels of the apparatus;
    c) analyzing said one or more samples using said apparatus.

18. The method of claim 17, wherein said analyte is selected from the group consisting of a protein, peptide, carbohydrate, polysaccharide, glycoprotein, lipid, hormone, growth factor, cytokine, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal, virus, bacterium, Salmonella, Streptococcus, Legionella, *E. coli*, Giardia, Cryptosporidium, Rickettsia, spore, mold, yeast, algae, amoebae, dinoflagellate, unicellular organism, pathogen and cell.

19. The method of claim 17, wherein said sample is an environmental, clinical, veterinary, pathologic or medical sample.

* * * * *